United States Patent
Li et al.

(10) Patent No.: US 12,364,695 B2
(45) Date of Patent: *Jul. 22, 2025

(54) METHODS OF TREATING INFLAMMATORY DISEASE

(71) Applicant: INTRA-CELLULAR THERAPIES, INC., New York, NY (US)

(72) Inventors: Peng Li, New Milford, NJ (US); Robert E. Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 147 days.

This patent is subject to a terminal disclaimer.

(21) Appl. No.: 17/336,798

(22) Filed: Jun. 2, 2021

(65) Prior Publication Data

US 2021/0369715 A1    Dec. 2, 2021

Related U.S. Application Data

(60) Provisional application No. 63/033,706, filed on Jun. 2, 2020.

(51) Int. Cl.
    *A61K 31/519*      (2006.01)
    *A61K 45/06*      (2006.01)

(52) U.S. Cl.
    CPC ............ *A61K 31/519* (2013.01); *A61K 45/06* (2013.01)

(58) Field of Classification Search
    CPC .. A61K 31/4015; A61K 31/519; A61K 45/06; A61P 31/14; A61P 29/00
    See application file for complete search history.

(56) References Cited

U.S. PATENT DOCUMENTS

| | | | |
|---|---|---|---|
| 4,469,868 | A | 9/1984 | de Wald |
| 4,603,203 | A | 7/1986 | Furukawa et al. |
| 4,666,908 | A | 5/1987 | Hamilton |
| 4,690,935 | A | 9/1987 | Taylor et al. |
| 5,202,328 | A | 4/1993 | de Laszlo et al. |
| 5,294,612 | A | 3/1994 | Bacon et al. |
| 5,393,755 | A | 2/1995 | Neustadt et al. |
| 5,824,683 | A | 10/1998 | McKittrick et al. |
| 5,849,770 | A | 12/1998 | Head et al. |
| 5,939,419 | A | 8/1999 | Tulshian et al. |
| 5,962,492 | A | 10/1999 | Warrellow et al. |
| 6,013,621 | A | 1/2000 | Nishi et al. |
| 6,028,074 | A | 2/2000 | Cheshire et al. |

(Continued)

FOREIGN PATENT DOCUMENTS

| | | |
|---|---|---|
| DE | 19931206 A1 | 1/2001 |
| EP | 0063381 A1 | 10/1982 |

(Continued)

OTHER PUBLICATIONS

Ye et al., Journal of Infection, vol. 80, pp. 607-613, publ. online Apr. 10, 2020 (Year: 2020).*

(Continued)

*Primary Examiner* — Sarah Pihonak
(74) *Attorney, Agent, or Firm* — Hoxie & Associates LLC

(57) ABSTRACT

The disclosure provides the administration of inhibitors of phosphodiesterase 1 (PDE1) for the treatment and prophylaxis of diseases or disorders characterized by inflammation, including methods of treatment and pharmaceutical compositions for use therein.

7 Claims, 7 Drawing Sheets

(56) References Cited

U.S. PATENT DOCUMENTS

| | | | |
|---|---|---|---|
| 6,133,273 | A | 10/2000 | Gilbert et al. |
| 6,235,742 | B1 | 5/2001 | Bell et al. |
| 6,235,746 | B1 | 5/2001 | Davis et al. |
| 6,316,444 | B1 | 11/2001 | Hunt et al. |
| 6,423,716 | B1 | 7/2002 | Matsuno et al. |
| 6,492,371 | B2 | 12/2002 | Roylance |
| 6,498,165 | B1 | 12/2002 | Armstrong et al. |
| 6,552,029 | B1 | 4/2003 | Davis et al. |
| 6,586,423 | B2 | 7/2003 | Bilodeau et al. |
| 6,599,908 | B1 | 7/2003 | Davis et al. |
| 6,649,608 | B2 | 11/2003 | Pease et al. |
| 6,670,368 | B1 | 12/2003 | Breault et al. |
| 6,693,099 | B2 | 2/2004 | Degenhardt et al. |
| 6,756,373 | B1 | 6/2004 | Allerton et al. |
| 6,943,171 | B2 | 9/2005 | Asberom et al. |
| 6,969,719 | B2 | 11/2005 | Asberom et al. |
| 7,153,824 | B2 | 12/2006 | Palmer et al. |
| 7,157,451 | B2 | 1/2007 | Atwal et al. |
| 7,285,558 | B2 | 10/2007 | Basarab et al. |
| 7,528,148 | B2 | 5/2009 | Allen et al. |
| 7,579,324 | B2 | 8/2009 | Burnet et al. |
| 7,666,843 | B2 | 2/2010 | Benowitz et al. |
| 8,273,750 | B2 | 9/2012 | Li et al. |
| 8,273,751 | B2 | 9/2012 | Li |
| 8,536,159 | B2 | 9/2013 | Li et al. |
| 8,633,180 | B2 | 1/2014 | Li et al. |
| 8,648,085 | B2 | 2/2014 | Eickmeier et al. |
| 8,664,207 | B2 | 3/2014 | Li et al. |
| 8,697,710 | B2 | 4/2014 | Li et al. |
| 8,829,008 | B2 | 9/2014 | Li |
| 8,846,693 | B2 | 9/2014 | Li et al. |
| 8,858,911 | B2 | 10/2014 | Li et al. |
| 8,859,564 | B2 | 10/2014 | Li et al. |
| 8,927,556 | B2 | 1/2015 | Li et al. |
| 9,000,001 | B2 | 4/2015 | Li et al. |
| 9,006,258 | B2 | 4/2015 | Fienberg et al. |
| 9,073,936 | B2 | 7/2015 | Li et al. |
| 9,157,906 | B2 | 10/2015 | Greengard et al. |
| 9,198,924 | B2 | 12/2015 | Mates et al. |
| 9,255,099 | B2 | 2/2016 | Li et al. |
| 9,371,327 | B2 | 6/2016 | Li et al. |
| 9,403,836 | B2 | 8/2016 | Li |
| 9,434,730 | B2 | 9/2016 | Li et al. |
| 9,468,637 | B2 | 10/2016 | Fienberg et al. |
| 9,469,647 | B2 | 10/2016 | Li et al. |
| 9,545,406 | B2 | 1/2017 | Wennogle |
| 9,556,185 | B2 | 1/2017 | Li et al. |
| 9,556,186 | B2 | 1/2017 | Li et al. |
| 9,598,426 | B2 | 3/2017 | Li et al. |
| 9,624,230 | B2 | 4/2017 | Li et al. |
| 9,757,424 | B2 | 9/2017 | Halse et al. |
| 9,763,948 | B2 | 9/2017 | Li et al. |
| 9,849,132 | B2 | 12/2017 | Hendrick et al. |
| 9,884,872 | B2 | 2/2018 | Li |
| 10,150,774 | B2 | 12/2018 | Li et al. |
| 10,183,023 | B2 | 1/2019 | Wennogle |
| 10,300,064 | B2 | 5/2019 | Li et al. |
| 10,561,656 | B2 | 2/2020 | Li et al. |
| 10,682,355 | B2 | 6/2020 | Wennogle |
| 11,291,666 | B2 | 4/2022 | Snyder et al. |
| 11,464,781 | B2 | 10/2022 | Davis et al. |
| 11,504,372 | B2 | 11/2022 | Wennogle |
| 2003/0069246 | A1 | 4/2003 | Darrow et al. |
| 2003/0092908 | A1 | 5/2003 | Pitts et al. |
| 2003/0162782 | A1 | 8/2003 | Grossman et al. |
| 2005/0075795 | A1 | 4/2005 | Pandit |
| 2005/0113379 | A1 | 5/2005 | Ge et al. |
| 2005/0287665 | A1 | 12/2005 | Cheng et al. |
| 2007/0155662 | A1 | 7/2007 | Golz et al. |
| 2007/0286890 | A1 | 12/2007 | Walt |
| 2008/0176961 | A1 | 7/2008 | Greengard et al. |
| 2008/0193964 | A1 | 8/2008 | Greengard et al. |
| 2008/0194592 | A1 | 8/2008 | Mates et al. |
| 2011/0217301 | A1* | 9/2011 | Freishtat .............. A61K 31/343 435/375 |
| 2013/0045988 | A1 | 2/2013 | Lefebvre et al. |
| 2014/0005155 | A1 | 1/2014 | Li et al. |
| 2014/0011783 | A1 | 1/2014 | Li et al. |
| 2014/0128353 | A1 | 5/2014 | Bannister et al. |
| 2014/0148421 | A1 | 5/2014 | Li et al. |
| 2015/0017267 | A1 | 1/2015 | Guedes et al. |
| 2015/0038474 | A1 | 2/2015 | Li et al. |
| 2015/0072965 | A1 | 3/2015 | Li et al. |
| 2015/0080357 | A1 | 3/2015 | Li et al. |
| 2016/0083390 | A1 | 3/2016 | Li et al. |
| 2016/0362489 | A1 | 12/2016 | Yang |
| 2019/0292246 | A1 | 9/2019 | Levitsky |
| 2021/0338679 | A1 | 11/2021 | Li et al. |
| 2022/0072003 | A1 | 3/2022 | Snyder et al. |
| 2023/0183239 | A1 | 6/2023 | Gallatin et al. |

FOREIGN PATENT DOCUMENTS

| | | | | |
|---|---|---|---|---|
| EP | 0636626 | A1 | 2/1995 | |
| WO | 1998/052568 | A1 | 11/1998 | |
| WO | 2001/027113 | A2 | 4/2001 | |
| WO | 2002/074312 | A1 | 9/2002 | |
| WO | 2004/031375 | A2 | 4/2004 | |
| WO | 2006/029257 | A2 | 3/2006 | |
| WO | WO-2009075784 | A1 * | 6/2009 | ........... A61K 31/519 |
| WO | WO 2010/065148 | A1 | 6/2010 | |
| WO | WO 2014/151409 | A1 | 9/2014 | |
| WO | WO 2018-049417 | A1 | 3/2018 | |
| WO | WO 2020/069043 | A1 | 4/2020 | |
| WO | WO-2021194893 | A1 * | 9/2021 | .............. A61P 11/00 |

OTHER PUBLICATIONS

Ogier et al., Brain, Behavior, & Immunity, vol. 5, pp. 1-7, publ. May 15, 2020 (Year: 2020).*

Li et al., Lancet, vol. 395, pp. 1517-1520, publ. Apr. 17, 2020 (Year: 2020).*

Intra-Cellular Therapies, Inc., "Corporate Presentation," (Sep. 24, 2019) downloaded from https://ir.intracellulartherapies.com/static-files/93b08960-f01c-4864-aa22-8cadb3539753, last accessed on May 8, 2023.

Martinez et al., "Genetic Programs Expressed in Resting and IL-4 Alternatively Activated Mouse and Human Macrophages: Similarities and Differences," Blood, vol. 121, No. 9, 13 pages, (2013).

Mietto et al., "Role of IL-10 in Resolution of Inflammation and Functional Recovery after Peripheral Nerve Injury," The Journal of Neuroscience, vol. 35, No. 50, p. 16431-16442, (2015).

"Anxiety," [retrieved on May 14, 2008]. Retrieved online via Internet, URL: http://www.nlm.nih.gov/medlineplus/anxiety.html, 5 pages.

"Autism," [retrieved on May 14, 2008]. Retrieved online via Internet, URL: http://www.nlm.nih.gov/medlineplus/autism.html, 6 pages.

"Gene expression," Wikipedia, 17 pages, (2017); accessed on Jul. 18, 2019 at https://en.wikipedia.org/w/index.php?title=Gene_expression&oldid=803718522.

Abdel-Wahab, N. et al., "Adverse Events Associated with Immune Checkpoint Blockade in Patients with Cancer: A Systematic Review of Case Reports," PLOS One, vol. 11, No. 7, 15 pages, (2016).

Abusnina, A. et al., "Anti-proliferative Effect of Curcumin on Melanoma Cells is Mediated by PDE1A Inhibition that Regulates the Epigenetic Integrator UHRF1," Mol. Nutr. Food Res., vol. 55, pp. 1677-1689, (2011); doi: 10.1002/mnfr.201100307.

Ahlström, M., et al. "Cyclic Nucleotide Phosphodiesterases (PDEs) in Human Osteoblastic Cells; The Effect of PDE Inhibition on cAMP Accumulation," Cell Mol Biol Lett, vol. 10, No. 2, pp. 305-319, (2005).

Ahmad, F. et al., "Cyclic Nucleotide Phosphodiesterases: Important Signaling Modulators and Therapeutic Targets," Oral Diseases, vol. 21, pp. e25-e50, (2015); doi: 10.1111/odi.12275.

Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, vol. 40, No. 14, pp. 2196-2210, (1997).

(56) References Cited

OTHER PUBLICATIONS

Al-Faleq, E. et al., "Heterocyclic o-Aminonitriles: Preparation of Pyrazolo [3,4-d]-pyrimidines with Modification of the substituents at the 1-position," Molecules, vol. 6, pp. 621-638, (2001).
Almahariq, M. et al., "Pharmacological Inhibition and Genetic Knockdown of Exchange Protein Directly Activated by cAMP 1 Reduce Pancreatic Cancer Metastasis in Vivo," Molecular Pharmacology, vol. 87, No. 2, pp. 142-149, (2015), DOI: https://doi.org/10.1124/mol.114.095158.
Argyle, D. et al., "Targeting Macrophage-Recruiting Chemokines as a Novel Therapeutic Strategy to Prevent the Progression of Solid Tumors," Frontiers in Immunology, vol. 9, Article 2629, 15 pages, (2018); doi: 10.3389/fimmu.2018.02629.
Aswar, M. et al., "Anti-Cataleptic Activity of Various Extracts of Ocimum Sanctum," International Journal of Pharmaceutical Research and Development, vol. 2, No. 6, 7 pages, (2010).
Banker, G. et al., Modern Pharmaceutics, Third Edition, Marcel Dekker Inc., New York, 3 pages, (1996).
Bastia, E. et al., "Effect of A1 and A2A Adenosine Receptor Ligands in Mouse Acute Models of Pain," Neuroscience Letters, vol. 328, pp. 241-244, (2002).
Bender et al., "Cyclic Nucleotide Phosphodiesterases: Molecular Regulation to Clinical Use," Pharmacological Reviews, vol. 58, No. 3, p. 488-520, (2006).
Blokland et al., "PDE Inhibition and Cognition Enhancement," vol. 22, No. 4, p. 349-354, (2012); Abstract Only.
Boyd et al., "cAMP-Phosphodiesterase PDE4D as a Target for Colon Cancer Therapy," The FASEB Journal, vol. 31, No. 1, 2 pages, (2017).
Boyd et al., "Dopamine Receptor Signaling and Current and Future Antipsychotic Drugs" in Current Antipsychotics, Handbook of Experimental Pharmacology, vol. 212, Gross, G. et al., Eds., doi:10.1007/978-3-642-25761-2_3, Springer-Verlag, Berlin, pp. 53-86, (2012).
Brodbelt et al., "Glioblastoma in England: 2007-2011," Eur J Cancer, vol. 51, pp. 533-542, (2015).
Burnouf et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, vol. 43, No. 25, p. 4850-4867, (2000).
Chalimoniuk et al., "Upregulation of Guanylyl Cyclase Expression and Activity in Striatum of MPTP-induced Parkinsonism in Mice," Biochemical and Biophysical Research Communications, vol. 324, p. 118-126, (2004).
Chebib et al., "1-Phenylpyrazolo[3,4-d]pyrimidines; Structure-Activity Relationships for C6 Substituents at A1 and A2A Adenosine Receptors," Bioorganic & Medicinal Chemistry, vol. 8, p. 2581-2590, (2000).
Chen et al., "Broad Spectrum neuroprotection profile of phosphodiesterase inhibitos as related to modulation of cell-cucle elements and caspase-3 activation," Neuroscience Letters, vol. 418, pp. 165-169, (2007).
Chen et al., "cAMP Inhibits Cell Migration by Interfering with Rac-induced Lamellipodium Formation," Journal of Biological Chemistry, vol. 283, No. 20, pp. 13799-13805, (2008), DOI: 10.1074/jbc.M800555200.
Chen et al., "Effects of Bimatoprost 0.03% on Ocular Hemodynamics in Normal Tension Glaucoma," Journal of Ocular Pharmacology and Therapeutics, vol. 22, No. 3, p. 188-193, (2006).
Chermat et al., "Adaptation of the Tail Suspension Test to the Rat," Journal de Pharmacologie (Paris), vol. 17. No. 3, p. 348-350, (1986).
Coussens et al., "Inflammation and Cancer," Nature, vol. 420, No. 6917, pp. 860-867, (2002), DOI: 10.1038/nature01322.
Daniel et al., "Sensitivity of GBM Cells to cAMP Agonist-mediated Apoptosis Correlates with CD44 Expression and Agonist Resistance with MAPK Signaling," Cell Death and Disease, vol. 7, No. e2494, 11 pages, (2016), DOI: 10.1038/cddis.2016.393.
Daviglus et al., "National Institutes of Health State-of-the-Science Conference Statement: Preventing Alzheimer Disease and Cognitive Decline," Annals of Internal Medicine, vol. 153, No. 3, pp. 176-185, (2010).
Deshmukh et al., "Amelioration of Intracerebroventricular Streptozotocin Induced Cognitive Dysfunction and Oxidative Stress by Vinpocetine—A PDE1 Inhibitor," European Journal of Pharmacology, vol. 620, No. 1-3, p. 49-56, (2009).
Dewald et al., "Synthesis and Potential Antipsychotic Activity of 1H-Imidazo[1,2-c]pyrazolo[3,4-e]pyrimidines," Journal of Medicinal Chemistry, vol. 31, p. 454-461, (1988).
Ehrman et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, vol. 5, No. 7, p. 540-551, (2006).
Ennaceur et al., "A New One-Trial Test for Neurobiological Studies of Memory in Rats. 1:Behavioral Data," Behavioural Brain Research, vol. 31, p. 47-59, (1998).
Fienberg et al., "DARPP-32: Regulator of the Efficacy of Dopaminergic Neurotransmission," Science, vol. 281, p. 838-842, (1998).
Filgueiras et al., "Phosphodiesterase Type 1 Inhibition Improves Learning in Rats Exposed to Alcohol During the Third Trimester Equivalent of Human Gestation," Neuroscience Letters, vol. 473, No. 3, p. 202-207, (2010).
Gelbin et al., "Ketene-S,N-acetals as Synthons for Heterocycles, New Synthesis of Pyrimidinones," Journal Für Praktische Chemie, vol. 329, No. 5, p. 753-766, (1987).
Ghorab et al., "Synthesis, Anticancer and Radioprotective Activities of Some New Pyrazolo[3,4-d]pyrimidines Containing Amino Acid Moieties," Arzneimittelforschung, vol. 59, No. 2, p. 96-103, (2009).
Goodman & Gilman, The Pharmacological Basis of Therapeutics, McGraw-Hill Interamericana, p. 892, (2007).
Greengard et al., "Beyond the Dopamine Receptor: The DARPP-32/Protein Phosphatase-1 Cascade," Neuron, vol. 23, p. 435-447, (1999).
Han et al., "The Calcium/Calmodulin-dependent Phosphodiesterase PDE1C Down-regulates Glucose-induced Insulin Secretion," The Journal of Biological Chemistry, vol. 274, No. 32, p. 22337-22344, (1999).
Hebb et al., "Role of Phosphodiesterases in Neurological and Psychiatric Disease," Current Opinion in Pharmacology, vol. 7, pp. 86-92, (2007).
Hulley et al., "Cyclic AMP Promotes the Survival of Dopaminergic Neurons in vitro and Protects Them from the Toxic Effects of MPP+," Journal of Neural Transmission [Supplemental], vol. 46, p. 217-228, (1995).
Insel et al., "Cyclic AMP is Both a Pro-apoptotic and Anti-apoptotic Second Messenger," Acta Physiol (Oxf), vol. 204, No. 2, pp. 277-287, (2012), DOI: 10.1111/j.1748-1716.2011.02273.x.
International Search Report for International Application No. PCT/US2014/025666 mailed Jul. 7, 2014, 3 pages.
International Search Report of International Application No. PCT/US2006/022066, mailed Apr. 3, 2007, 1 page.
International Search Report of International Application No. PCT/US2008/013411, mailed Mar. 19, 2009, 2 pages.
International Search Report of International Application No. PCT/US2014/030412, mailed Nov. 6, 2014, 3 pages.
International Search Report of International Application No. PCT/US2017/051220, mailed Nov. 22, 2017, 3 pages.
Jang, I-K., et al. "Adaptation of cAMP Signaling System in SH-SY5Y Neuroblastoma Cells Following Expression of a Constitutively Active Stimulatory G Protein Alpha, Q227L Gsα," Exp Mol Med, vol. 33, No. 1, pp. 37-45, (2001).
Ji et al., "Efficacy of vinpocetine on neuropathy in patients with type 2 diabetes mellitus," Chinese Journal of New Drugs, vol. 18, No. 15, pp. 1415-1418, (2009).
Jiang et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, vol. 70, p. 2824-2827, (2005).

(56) References Cited

OTHER PUBLICATIONS

Jiang, X., et al. "Expression and Regulation of mRNA for Distinct Isoforms of cAMP-Specific PDE-4 in Mitogen-Stimulated and Leukemic Human Lymphocytes," Cell Biochem and Biophys, vol. 28, pp. 135-160, (1998).
Kakkar et al. "Amantadine: An Antiparkinsonian Agent Inhibits Bovine Brain 60 kDa Calmodulin-Dependent Cyclic Nucleotide Phosphodiesterase Isozyme," Brain Research, vol. 749, No. 2, p. 290-294, (1997).
Kakkar et al. "Calmodulin-dependent Cyclic Nucleotide Phosphodiesterase (PDE1)," CMLS Cellular and Molecular Life Sciences, vol. 55, No. 8-9, p. 1164-1186, (1999).
Kakkar et al., "Inhibition of Bovine Brain Calmodulin-Dependent Cyclic Nucleotide Phosphodiesterase Isozymes by Deprenyl," Life Sciences, vol. 59, No. 21, p. 337-341, (1996).
Kim et al., "Antiinflammatory cAMP Signaling and Cell Migration Genes Co-opted by the Anthrax Bacillus," PNAS, vol. 105, No. 16, pp. 6150-6155, (2008).
Klaissle et al., "Physical Activity and Environmental Enrichment Regulate the Generation of Neural Precursors in the Adult Mouse Substantia Nigra in a Dopamine-dependent Manner," BMC Neuroscience, vol. 13, No. 132, doi:10.1186/1471-2202-13-132, 15 pages, (2012).
Kleppisch, T., "Phosphodiesterases in the Central Nervous System" in cGMP: Generators, Effectors and Therapuetic Implications, Handbook of Experimental Pharmacology, vol. 191, Schmidt, H. et al., Eds., Springer-Verlag, Berlin, p. 71-92, (2009).
Koelzer et al., "Systemic inflammation in a melanoma patient treated with immune checkpoint inhibitors—an autopsy study," Journal for Immuno Therapy of Cancer, vol. 4, No. 13, pp. 1-8, (2016).
Kraft et al., "The phosphodiesterase-4 inhibitor rolipram protects from ischemic stroke in mice by reducing blood-brain-barrier damage, inflammation and thrombosis," vol. 247, pp. 80-90, (2013).
Laddha et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, vol. 17, No. 19, p. 6796-6802, (2009).
Li, P. et al., "Discovery of Potent and Selective Inhibitors of Phosphodiesterase 1 for the Treatment of Cognitive Impairment Associated with Neurodegenerative and Neuropsychiatric Diseases," Journal of Medicinal Chemistry, vol. 59, No. 3, pp. 1149-1164, (2016).
Lundqvist et al., "Exploitation of Structural and Regulatory Diversity in Glutamate Racemases," Nature, vol. 447, p. 817-822, (2007).
Mani et al., "Requirement for DARPP-32 in Progesterone-Facilitated Sexual Receptivity in Female Rats and Mice," Science, vol. 287, p. 1053-1056, (2000).
Marko, D., et al. "Cyclic 3',5'-nucleotide Phosphodiesterases: Potential Targets for Anticancer Therapy," Chem Res Toxicol, vol. 13, pp. 944-948, (2000).
Medina, A., "Therapeutic Utility of Phosphodiesterase Type I Inhibitors in Neurological Conditions," Frontiers in Neuroscience, vol. 5, No. 21, pp. 1-5, (2011).
Murray et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, vol. 292, p. L294-L303, (2007).
Murray et al., "LY503430, A Novel -Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, vol. 306, No. 2, p. 752-762, (2003).
Na et al., "The Role of Pro-Inflammatory Cytokines in the Neuroinflammation and Neurogenesis of Schizophrenia," Progress in Neuro-Psychopharmacology & Biological Psychiatry, vol. 48, pp. 277-286, (2014).
Nishi et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, vol. 114, p. 6-16, (2010).
Noguchi et al., "A Facile Preparation of 7-(Substituted Amino-)-6H-pyrrolo[3,4-d]-pyrimidine Derivatives," Bulletin of the Chemical Society of Japan, vol. 62, No. 9, p. 3043-3045, (1989).
Pantziarka et al., "Repurposing Drugs in Oncology (ReDO)—Selective PDE5 Inhibitors as Anti-Cancer Agents," ECancer, vol. 12, No. 824, 22 pages, (2018).
Pardo et al., "Synthesis of 1-(p-Nitrobenzyl)Azoles and 1-(p-Nitrobenzyl)Benzazoles," OPPI Briefs, vol. 32, No. 4, p. 385-390, (2000).
Park et al., "Traumatic Brain Injury: Can the Consequences Be Stopped?" CMAJ, vol. 178, No. 9, p. 1163-1170, (2008).
Patani et al., "Bioisosterism: A Rational Approach in Drug Design," Chemical Reviews, vol. 96, No. 8, p. 3147-3716, (1996).
Peng et al., "Inhibitors of Phosphodiesterase as Cancer Therapeutics," European Journal of Medicinal Chemistry, vol. 150, pp. 742-756, (2018).
Polli et al., "Expression of a Calmodulin-dependent Phosphodiesterase Isoform (PDE1B1) Correlates With Brain Regions Having Extensive Dopaminergic Innervation," The Journal of Neuroscience, vol. 14, No. 3, p. 1251-1261, (1994).
Porsolt et al., "Depression: A New Animal Model Sensitive to Antidepressant Treatments," Nature, vol. 266, p. 730-732, (1977).
Poulsen et al., "High-Pressure Synthesis of Enantiomerically Pure C-6 Substituted Pyrazolo[3,4-d]pyrimidines," Biorganic & Medicinal Chemistry Letters, vol. 11, p. 191-193, (2001).
Prickaerts et al., "Possible Role of Nitric Oxide-Cyclic GMP Pathway in Object Recognition Memory: Effects of 7-Nitroindazole and Zaprinast," European Journal of Pharmacology, vol. 337, p. 125-136, (1997).
Reed et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, vol. 22, No. 12, p. 5188-5197, (2002).
Rowther, F. et al., "Cyclic nucleotide phosphodiesterase-1C (PDE1C) drives cell proliferation, migration and invasion in glioblastoma multiforme cells in vitro," Molecular Carcinogenesis, vol. 55, No. 3, pp. 268-279, (2016).
Rybalkin, S. et al., "Calmodulin-stimulated Cyclic Nucleotide Phosphodiesterase (PDE1C) is Induced in Human Arterial Smooth Muscle Cells of the Synthetic, Proliferative Phenotype," J Clin Invest, vol. 100, No. 10, pp. 2611-2621, (1997).
Rybalkin, S. et al., "Cyclic GMP Phosphodiesterases and Regulation of Smooth Muscle Function," Circulation Research, vol. 93, pp. 280-291, (2003).
Savai, R., et al. "Targeting cancer with phosphodiesterase inhibitors," Expert Opin. Investig. Drugs, vol. 19, No. 1, pp. 117-131, (2010).
Schmidt, C., "Phosphodiesterase Inhibitors as Potential Cognition Enhancing Agents," Current Topics in Medicinal Chemistry, vol. 10, No. 2, p. 222-230, (2010).
Sharma, R. et al., "Regulation of Calmodulin-Stimulated Cyclic Nucleotide Phosphodiesterase (PDE1): Review," International Journal of Molecular Medicine, vol. 18, p. 95-105, (2006).
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium," Cancer Research, vol. 64, p. 2568-2571, (2004).
Shimizu, K. et al., "Characterization of Phosphodiesterase 1 in Human Malignant Melanoma Cell Lines," AntiCancer Research, vol. 29, pp. 1119-1122, (2009).
Shiri, S. et al., "Dendrosomal Curcumin Suppresses Metastatic Breast Cancer in Mice by Changing M1/M2 Macrophage Balance in the Tumor Microenvironment," Asian Pac J Cancer Prev., vol. 16, No. 9, pp. 3917-3922, (2015).

(56) References Cited

OTHER PUBLICATIONS

Shook, B. et al., "Design and Characterization of Optimized Adenosine A2A/A1 Receptor Antagonists for the Treatment of Parkinson's Disease," Journal of Medicinal Chemistry, doi:10.1021/jm201640m, 47 pages, (2012).
Silva, A. et al., "Advances in Prodrug Design," Mini-Reviews in Medicinal Chemistry, vol. 5, pp. 893-914, (2005).
Snyder, G. et al., "Preclinical Profile of ITI-214, an Inhibitor of Phosphodiesterase 1, for Enhancement of Memory Performance in Rats," Psychopharmacology, vol. 213, pp. 3113-3124, (2016).
Soon, L., "A Discourse on Cancer Cell Chemotaxis: Where to From Here?", IUBMB Life, vol. 59, No. 2, pp. 60-67, (2007), DOI: 10.1080/15216540701201033.
Stupp, R. et al., "Radiotherapy Plus Concomitant and Adjuvant Temozolomide for Glioblastoma", N Engl J Med, vol. 352, No. 10, pp. 987-996, (2005).
Takahashi, A. et al., "Measurement of Intracellular Calcium," Physiological Reviews, vol. 79, No. 4, pp. 1089-1125, (1999).
Takimoto, E., "Controlling Myocyte cGMP, Phosphodiesterase 1 Joins the Fray," Circulation Research, vol. 105, p. 931-933, (2009).
Touat, M., et al. "Glioblastoma Targeted Therapy: Updated Approaches from Recent Biological Insights," Ann. Oncol., vol. 28, No. 7, pp. 1457-1472, (2017).
Turko, I. et al., "Inhibition of Cyclic GMP-Binding Cyclic GMP-Specific Phosphodiesterase (Type 5) by Sildenafil and Related Compounds," Molecular Pharmacology, vol. 56, pp. 124-130, (1999).
Ungerstedt, U. et al., "Quantitative Recording of Rotational Behavior in Rats After 6-Hydroxy-dopamine Lesions of the Nigrostriatal Dopamine System," Brain Research, vol. 24, pp. 485-493, (1970).
Ungerstedt, U., "Stereotaxic Mapping of the Monoamine Pathways in the Rat Brain*," Acta Physiologica Scandinavica, Supplementum 367, p. 1-48, (1971).
Vatter, S. et al., "Differential Phosphodiesterase Expression and Cytosolic Ca2+ in Human CNS Tumour Cells and in Non-Malignant and Malignant Cells of Rat Origin," Journal of Neurochemistry, vol. 93, pp. 321-329, (2005).
Vitale, G. et al., "A New Therapeutic Strategy Against Cancer: cAMP Elevating Drugs and Leptin," Cancer Biology & Therapy, vol. 8, No. 12, pp. 1191-1193, (2009), DOI: 10.4161/cbt.8.12.8937.
Watanabe, Y., et al. "Phosphodiesterase 4 Regulates the Migration of B16-F10 Melanoma Cells," Exp Ther Med, vol. 4, pp. 205-210, (2012).
Wolff, M. Ed., Burger's Medicinal Chemistry and Drug Discovery, Fifth Edition, vol. I: Principles and Practice, John Wiley & Sons, New York, p. 975-977, (1995).
Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, vol. 40, pp. 4372-4377, (1997).
Youdim, M., "The Path from Anti Parkinson Drug Selegiline and Rasagiline to Multifunctional Neuroprotective Anti Alzheimer Drugs Ladostigil and M30," Current Alzheimer Research, vol. 3, p. 541-550, (2006).
Zong, H. et al., "The Cellular Origin for Malignant Glioma and Prospects for Clinical Advancements," Expert Rev Mol Diagn., vol. 12, No. 4, pp. 383-394, (2012), DOI: 10.1586/erm.12.30.
Bastin, R. et al., "Salt Selection and Optimized Procedures for Pharmaceutical New Chemical Entities," Organic Process and Research Development, vol. 4, No. 5, pp. 427-435, (2000).
Borrajo, A. et al., "Important role of microglia in HIV-1 associated neurocognitive disorders and the molecular pathways implicated in its pathogenesis," Annals of Medicine, vol. 53, No. 1, pp. 43-69, (2021), doi: 10.1080/07853890.2020.1814962.
Greenmyer, J. et al., "Primary Human Microglia are Phagocytically Active and Respond to Borrelia burgdorferi With Upregulation of Chemokines and Cytokines," Frontiers in Microbiology, vol. 9, No. 811, 11 pages, (2018), doi: 10.3389/fmicb.2018.00811.
Hayakawa, T. et al., "Enhanced anti-tumor effects of the PD-1/PD-L1 blockade by combining a highly absorptive form of NF-KB/STAT3 inhibitor curcumin," Journal for ImmunoTherapy of Cancer, vol. 2, Suppl. 3, p. P210, (2014).
Johnson, J. et al., "Curcumin for chemoprevention of colon cancer," Cancer Letters, vol. 255, pp. 170-181, (2007).
Levy, I. et al., "Phosphodiesterase Function and Endocrine Cells: Links to Human Disease and Roles in Tumor Development and Treatment," Current Opinion in Pharmacology, vol. 11, pp. 689-697, (2011).
Saqib, U. et al., "Phytochemicals as modulators of M1-M2 macrophages in inflammation," Oncotarget, vol. 9, No. 25, pp. 17937-17950, (2018).
Snyder, G. et al., "Suppression of CNS Inflammation by Phosphodiesterase-1 (PDE1) Inhibitors: Toward New Treatments for Neurodegenerative Diseases," Database Embase, Database Accession No. EMB-620612543, Alzheimer's Association International Conference AAIC 2017 in London, 2 pages, Abstract only.
Szajewska, H., "Evidence-based Medicine and Clinical Research: Both are Needed, Neither is Perfect," Annals of Nutrition and Metabolism, vol. 72, No. 3, pp. 13-23, (2018).
Wesserling, M. et al., "Will in Vitro Tests Replace Animal Models in Experimental Oncology?," Journal of Tissue Science and Engineering, vol. 2, No. 1, p. 102e, (2011), Abstract only.
Zhao, A. et al., "Recent Advances in the Study of Ca2+/CaM-activated Phosphodiesterases: Expression and Physiological Functions," Adv Second Messenger Phosphoprotein Res, vol. 31, pp. 237-251, (1997).

* cited by examiner

FIG. 11A
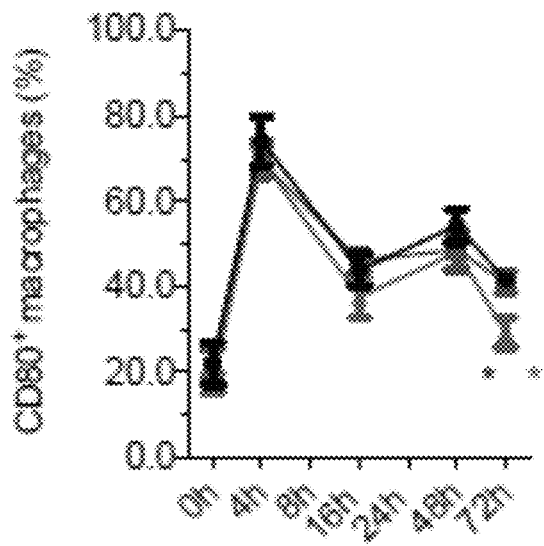
FIG. 11B
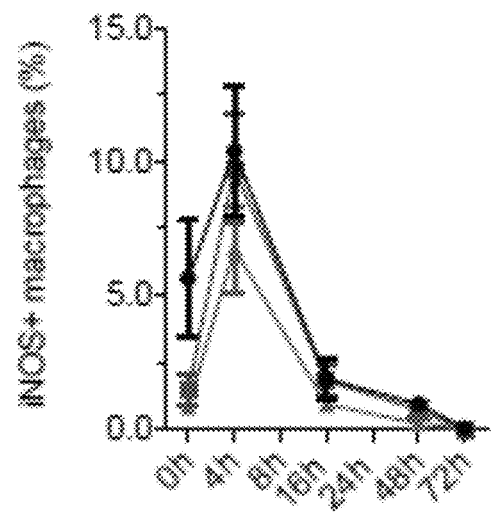
FIG. 12A
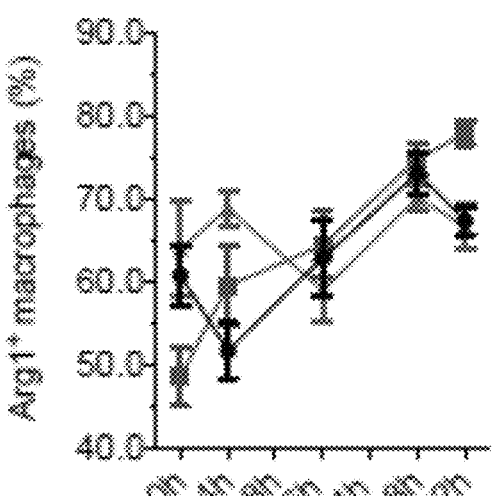
FIG. 12B

METHODS OF TREATING INFLAMMATORY DISEASE

CROSS-REFERENCE TO RELATED APPLICATIONS

This application claims priority to and the benefit of U.S. Provisional Application Ser. No. 63/033,706, filed on Jun. 2, 2020, the contents of which are hereby incorporated by reference in its entirety.

FIELD OF THE INVENTION

The field relates to the administration of inhibitors of phosphodiesterase 1 (PDE1) inhibitors for promoting the resolution of inflammation, for example through the polarization of M1 macrophages to M2 macrophage and microglia cells, and the treatment and prophylaxis of diseases or disorders related to inflammation.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), are activated by the $Ca^{2+}$-calmodulin and have been shown to mediate the calcium and cyclic nucleotide (e.g. cAMP and cGMP) signaling pathways. These PDEs are therefore active in stimulated conditions when intra-cellular calcium levels rise, leading to increased hydrolysis of cyclic nucleotides. The three known CaM-PDE genes, PDE1A, PDE1B, and PDE1C, are all expressed in central nervous system tissue. In the brain, the predominant expression of PDE1A is in the cortex and neostriatum, PDE1B is expressed in the neostriatum, prefrontal cortex, hippocampus, olfactory tubercle and immune cells, and PDE1C is more ubiquitously expressed.

PDE4 is the major cAMP-metabolizing enzyme found in inflammatory and immune cells, and PDE4 inhibitors are of interest as anti-inflammatory drugs. PDE1, however, has not been thought to play a major role in the inflammatory response, although PDE-1, in particular PDE1B, is induced in monocyte-to-macrophage differentiation mediated by the cytokine granulocyte-macrophage colony-stimulating factor (GM-CSF). The very weak PDE1 inhibitor vinpocetine has been shown have anti-inflammatory activity, but the anti-inflammatory action of vinpocetine is believed to be caused by a direct inhibition of the IκB kinase complex (IKK) rather than PDE1 blockade.

Macrophages have a central role in maintaining homeostasis and mediating inflammation in the body. Macrophages are capable of polarization by which a macrophage expresses different functional programs in response to microenvironmental signals. There are several activated forms of macrophages, but the two main groups are designated as M1 and M2. M1 macrophages, also referred to as "classically activated macrophages," are activated by LPS and IFN-gamma, and secrete high levels of IL-12 and low levels of IL-10 for a pro-inflammatory effect. In contrast, the M2 designation, also referred to as "alternatively activated macrophages," broadly refers to macrophages that function in constructive processes like wound healing and tissue repair, and those that turn off damaging immune system activation by producing anti-inflammatory cytokines like IL-10. M2 macrophages produce high levels of IL-10, TGF-beta and low levels of IL-12. Prolonged M1 type of macrophages is harmful for the organism and that is why tissue repair and restoration is necessary.

When tissues are challenged by pathogens, inflammatory monocytes in circulation are recruited and differentiated into macrophages. Generally, macrophages are polarized toward an M1 phenotype in the early stages of bacterial infection. For example, when bacteria are recognized by pathogen recognition receptors, macrophages are activated and produce a large amount of pro-inflammatory mediators including TNF-α, IL-1, and nitric oxide (NO), which kill the invading organisms and activate the adaptive immunity. For example, this mechanism has been considered to be involved in infection with *Salmonella typhi, Salmonella typhimurium, Listeria monocytogenes*, and the early phases of infection with *Mycobacterium tuberculosis, Mycobacterium ulcerans*, and *Mycobacterium avium*. If macrophage-mediated inflammatory response cannot be quickly controlled, a cytokine storm is formed, thereby contributing to the pathogenesis of severe sepsis. In order to counteract the excessive inflammatory response, macrophages undergo apoptosis or polarize to an M2 phenotype to protect the host from excessive injury and facilitate wound healing.

Macrophage polarization is also involved in virus infection, in which M2 phenotype macrophages can also suppress inflammation and promote tissue healing. Influenza virus augments the phagocytic function of human macrophages, which is a major feature of M2 phenotype, to clear apoptotic cells and accelerate the resolution of inflammation. In severe acute respiratory syndrome (SARS)-Cov infection, M2 phenotype macrophages are critical to regulate immune response and protect host from the long-term progression to fibrotic lung disease by a STAT dependent pathway. In addition, severe respiratory syncytial virus (RSV) induced bronchiolitis is closely associated with mixed M1 and M2 macrophages.

The pandemic of coronavirus disease 2019 (COVID-19) is caused by severe acute respiratory syndrome coronavirus 2 (SARS-CoV-2). This coronavirus can cause a respiratory syndrome which to date has affected thousands of individuals. Human coronavirus infections can induce not only mild to severe respiratory diseases, but also inflammation, high fever, cough, acute respiratory tract infection and dysfunction of internal organs that may lead to death. Coronavirus infections, regardless of the various types of corona virus, are primarily attacked by immune cells including mast cells (MCs), which are located in the submucosa of the respiratory tract and in the nasal cavity and represent a barrier of protection against microorganisms. Virally activated MCs release early inflammatory chemical compounds including histamine and protease; while late activation provoke the generation of pro-inflammatory IL-1 family members including IL-1, IL-6 and IL-33. It is believed that severe cases of SARS-CoV-2 is driven by uncontrolled immune-mediated inflammatory response.

The particular drivers of inflammation in COVID-19 are, at this time, poorly understood. It is believed that early activation of the immune system through the induction of a potent interferon response is important to control the virus. It has been theorized that a delayed interferon response may lead to progressive tissue damage, which ultimately leads to a deleterious hyperinflammation characterized in part by excessive macrophage activation that is seen in patients with severe disease. Bronchoalveolar fluid (BALF) from patients with severe COVID-19 was shown to be enriched in CCL2 and CCL7, two chemokines that are most potent at the recruitment of CC-chemokine receptor 2-positive (CCR2+) monocytes. BALF samples also revealed elevated proportions of mononuclear phagocytes characterized in part by an abundance of inflammatory monocyte-derived macrophages in patients with severe disease.

Severe cases of COVID-19 have been shown to result in systemic hyperinflammation designated under the umbrella term of macrophage activation syndrome (MAS) or cytokine storm, also known as secondary haemophagocytic lymphohistocytosis (sHLH). MAS is a severe, potentially fatal condition caused by excessive activation and expansion of macrophages and T cells, leading to an overwhelming inflammatory reaction. This hyperinflammation can lead to a host of complications for patients.

Inflammatory processes in general, and diseases and disorders related to inflammation, are numerous, and the mechanisms and actions are still not well understood. Currently, there is a largely unmet need for an effective way of treating inflammation and inflammatory related diseases and disorders.

SUMMARY OF THE INVENTION

The inventors have surprisingly discovered that PDE1 mediates the expression of certain pro-inflammatory cytokines and chemokines and that PDE1 inhibitors have specific anti-inflammatory effects. In one aspect, inhibition of PDE1 regulates inflammatory activity in macrophages, reducing expression of pro-inflammatory genes, thereby providing novel treatments for a variety of disorders and conditions characterized by macrophage mediation.

Positive regulation of inflammatory resolution responses in macrophages and microglia by elevated intracellular cyclic nucleotide levels provides a promising area for therapeutic intervention. It is known that PDE1B is present in monocytes and involved in the differentiation into macrophage via growth factor activation signals such as GM-CSF. Bender A T, et al., Selective up-regulation of PDE1B2 upon monocyte-to-macrophage differentiation, Proc Natl Acad Sci USA. 2005 Jan. 11; 102(2): 497-502. Cyclic guanosine monophosphate (cGMP) has been demonstrated to be a key modulator of the differentiation pathways in macrophages. cGMP also plays a role in modulation of inflammatory processes, such as inducible NO synthase induction and TNF-α release. Therefore, the marked up-regulation of PDE1B may be critical in the regulation of these processes in differentiated macrophages. This suggests that PDE1 inhibitors, such as those disclosed herein, may prove beneficial in diseases associated with, for example, inflammation disorders relating to macrophage activation.

In one embodiment, therefore, the invention provides using various PDE1 inhibitory compounds to treat inflammation, and/or diseases or disorders related to inflammation. Without being bound by theory, one possible mechanism for this activity is that inhibition of PDE1B may affect macrophage activation in the blood or tissue and/or microglial activation in the CNS, so as to reduce M1 activation and the release of pro-inflammatory cytokines, and to promote the polarization of macrophages to M2 type through the up-regulation of anti-inflammatory cytokines such as IL-10. Discussion of the treatment of and prophylaxis of inflammation and/or diseases or disorders related to inflammation as they relate to the microglia, e.g., neuroinflammation, is discussed in International Publication WO 2018/049417 A1, which is hereby incorporated by reference in its entirety. Further discussion of treatment of inflammatory related diseases, disorders and conditions as related to M1 macrophage activation is discussed in WO 2020/069043 A1, which is hereby incorporated by reference in its entirety.

The regulation of M1 to M2 type activation in macrophages is central to inflammatory pathways in a number of disorders. The role of M1 to M2 polarization in macrophages is important in a number of inflammatory-related disorders including viral infections, such as coronavirus infections (e.g., a Severe Acute Respiratory Syndrome Coronavirus (e.g., SARS-CoV, SARS-CoV-2), a Middle East Respiratory Syndrome coronavirus (MERS), 229E coronavirus, NL63 coronavirus, OC43 coronavirus, HKU1 coronavirus).

Targeted inhibition of PDE1 with a compound of the present invention is believed to affect macrophage activation and promote production of anti-inflammatory cytokines and factors involved in resolution of macrophage mediated hyperimmune responses.

Furthermore, PDE1 inhibitors are useful for inhibiting motility of immune system cells, including macrophages and microglia, recruited by inflammatory cytokines, as well as disruption of immune surveillance provided by the recruited cells. Since PDE1 inhibitory compounds inhibits not only CCL2 but also other cytokines and chemokines believed to be involved in this recruitment, it is believed that administration of a PDE1 inhibitor would also serve to prevent macrophage and microglia infiltration into the site of active inflammation.

Accordingly, in one aspect, the invention provides a method of promoting resolution of inflammation for the treatment or prophylaxis of a viral infection or an inflammatory disease, condition or disorder consequent to a viral infection, the method comprising administering a pharmaceutically effective amount of a specific inhibitor of phosphodiesterase type I (e.g., PDE1 inhibitor, e.g., a PDE1B inhibitor) (e.g., a PDE1 inhibitor of Formulas I, Ia, II, III, IV, V, and/or VI as herein described) to a patient in need thereof.

In another aspect, the invention provides a method of promoting macrophage activation to the M2 activation state in a patient suffering from a viral infection or an inflammatory disease, condition or disorder consequent to a viral infection, the method comprising administering a pharmaceutically effective amount of a specific inhibitor of phosphodiesterase type I (e.g., PDE1 inhibitor, e.g., a PDE1B inhibitor) (e.g., a PDE1 inhibitor of Formulas I, Ia, II, III, IV, V, and/or VI as herein described), e.g., an amount effective to promote macrophage activation from the M1 activation state to the M2 activation state in a patient in need thereof.

Further embodiments of the invention are set forth or evident from the detailed description below and the examples herein.

BRIEF DESCRIPTION OF DRAWINGS

FIG. 11A depicts the amount of CD80+ macrophages expressed as a percentage of total macrophages detected at the site of inflammation.

FIG. 11B depicts the amount of iNOS+ macrophages expressed as a percentage of total macrophages detected at the site of inflammation.

FIG. 12A depicts the amount of Arg1+ macrophages expressed as a percentage of total macrophages detected at the site of inflammation.

FIG. 12B depicts the amount of CD206+ macrophages expressed as a percentage of total macrophages detected at the site of inflammation.

DETAILED DESCRIPTION OF THE INVENTION

Figure 1:
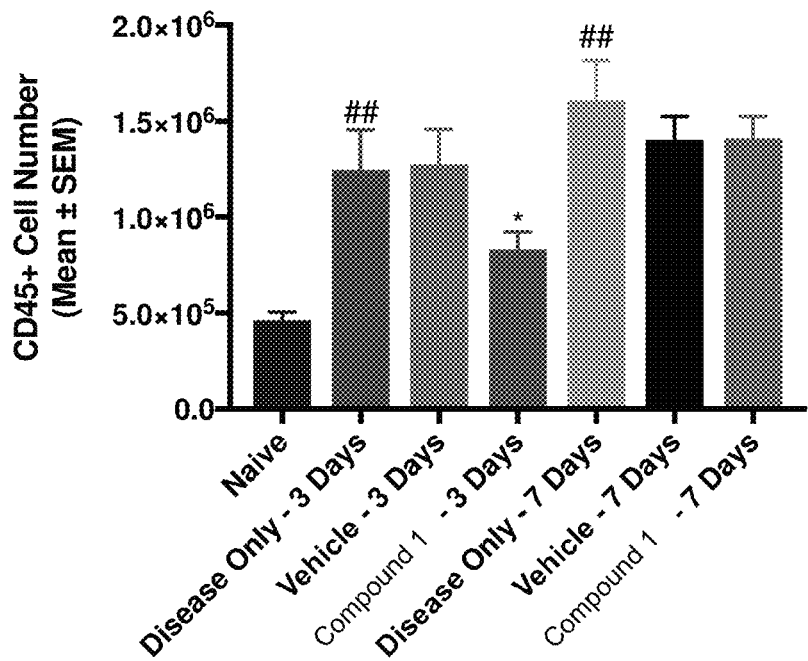
FIG. 1 depicts the number of leukocytes detected at the site of inflammation following sterile insult when treated with Compound 1.
Figure 2A:
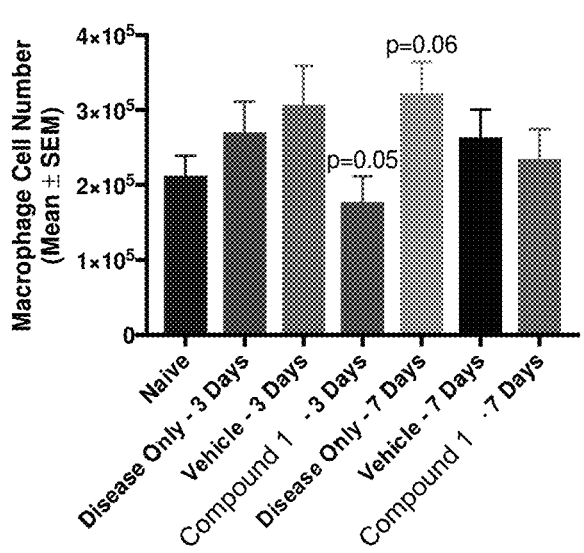
FIG. 2A depicts the number of macrophages detected at the site of inflammation following sterile insult when treated with Compound 1.
Figure 2B:
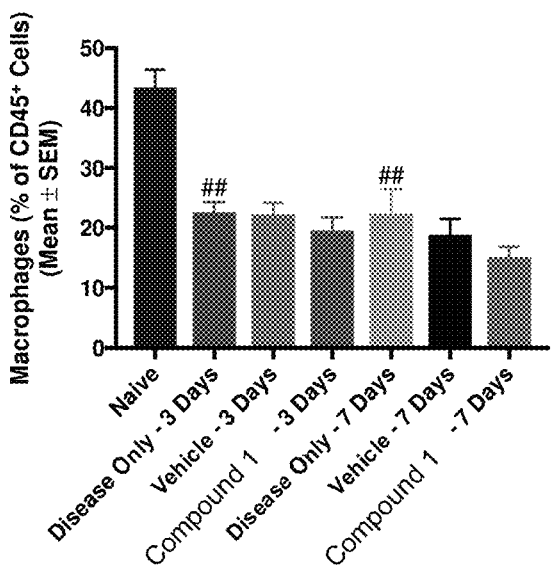
FIG. 2B depicts the number of macrophages expressed as percent of total leukocytes detected at the site of inflammation following sterile insult when treated with Compound 1.

Compounds for Use in the Methods of the Invention

In one embodiment, the PDE1 inhibitors for use in the methods of treatment and prophylaxis described herein are optionally substituted 7,8-dihydro-imidazo[1,2-a]pyrazolo[4,3-e]pyrimidin-4-one compounds and 7,8,9-trihydro-[1H or 2H]-pyrimido[1,2-a]pyrazolo[4,3-e]pyrimidin-4(5H)-one compounds, in free or pharmaceutically acceptable salt form.

In still yet another embodiment, the invention provides that the PDE1 inhibitors for use in the methods of treatment and prophylaxis which are described herein are selected from any of the Applicant's own publications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, and WO 2011/153138, the entire contents of each of which are incorporated herein by reference in their entireties.

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; and U.S. Publication 2017/0291901A1; each of which are incorporated by reference in their entirety. In any situation in which the statements of any documents incorporated by reference contradict or are incompatible with any statements made in the present disclosure, the statements of the present disclosure shall be understood as controlling.

In yet another embodiment the invention provides that the PDE1 inhibitors for use in the methods of treatment and prophylaxis described herein are compounds of Formula I:

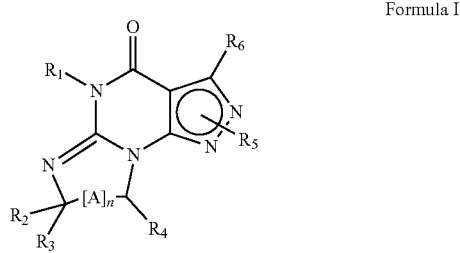

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl; or $R_5$ is attached to one of the nitrogens on the pyrazolo portion of Formula I and is a moiety of Formula A

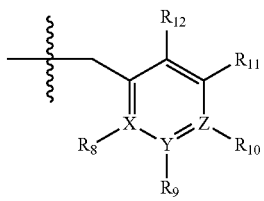

Formula A wherein X, Y and Z are, independently, N or C, and R₈, R₉, R₁₁ and R₁₂ are independently H or halogen (e.g., Cl or F), and R₁₀ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, R₈, R₉, or R₁₀, respectively, is not present; and (iv) R₆ is H, alkyl, aryl, heteroaryl, arylalkyl (e.g., benzyl), arylamino (e.g., phenylamino), hetarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;

(vi) when n=1, A is —C(R₁₃R₁₄)— wherein R₁₃ and R₁₄, are, independently, H or C₁₋₄ alkyl, aryl, heteroaryl, (optionally hetero)arylalkoxy or (optionally hetero)arylalkyl;

in free, salt or prodrug form, including its enantiomers, diastereoisomers and racemates.

In another embodiment the invention provides that the PDE1 inhibitors for use in the methods as described herein are Formula 1a:

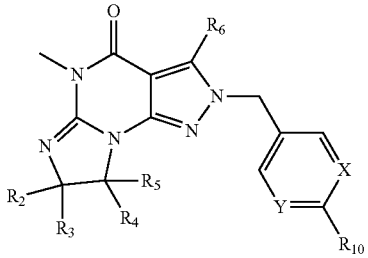

Formula Ia wherein (i) R₂ and R₅ are independently H or hydroxy and R₃ and R₄ together form a tri- or tetra-methylene bridge [pref. with the carbons carrying R₃ and R₄ having the R and S configuration respectively]; or R₂ and R₃ are each methyl and R₄ and R₅ are each H; or R₂, R₄ and R₅ are H and R₃ is isopropyl [pref. the carbon carrying R₃ having the R configuration];

(ii) R₆ is (optionally halo- or hydroxy-substituted) phenylamino, (optionally halo- or hydroxy-substituted) benzylamino, C₁₋₄alkyl, or C₁₋₄alkyl sulfide; for example phenylamino or 4-fluorophenylamino;

(iii) R₁₀ is C₁₋₄alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and X and Y are independently C or N, in free, pharmaceutically acceptable salt or prodrug form, including its enantiomers, diastereoisomers and racemates.

In another embodiment the invention provides that the PDE1 inhibitors for use in the methods of treatment and prophylaxis described herein are compounds of Formula II:

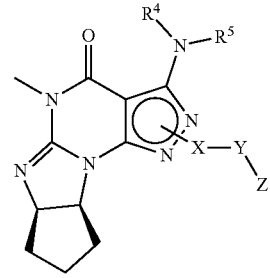

Formula II (i) X is C₁₋₆alkylene (e.g., methylene, ethylene or prop-2-yn-1-ylene);

(ii) Y is a single bond, alkynylene (e.g., —C≡C—), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), haloC₁₋₆alkyl (e.g., trifluoromethyl), —C(O)—R¹, —N(R²)(R³), or C₃₋₇cycloalkyl optionally containing at least one atom selected from a group consisting of N or O (e.g., cyclopentyl, cyclohexyl, tetrahydro-2H-pyran-4-yl, or morpholinyl);

(iv) R¹ is C₁₋₆alkyl, haloC₁₋₆alkyl, —OH or —OC₁₋₆alkyl (e.g., —OCH₃);

(v) R² and R³ are independently H or C₁₋₆alkyl;

(vi) R⁴ and R⁵ are independently H, C₁₋₆alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or C₁₋₆alkoxy;

(vii) wherein X, Y and Z are independently and optionally substituted with one or more halo (e.g., F, Cl or Br), C₁₋₆alkyl (e.g., methyl), haloC₁₋₆alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC₁₋₆alkyl (e.g., 5-trifluoromethylpyrid-2-yl) or C₁₋₆-alkyl (e.g., 5-methylpyrid-2-yl), or Z is aryl, e.g., phenyl, substituted with one or more halo (e.g., 4-fluorophenyl), in free, salt or prodrug form.

In yet another embodiment the invention provides that the PDE1 inhibitors for use in the methods of treatment and prophylaxis described herein are Formula III:

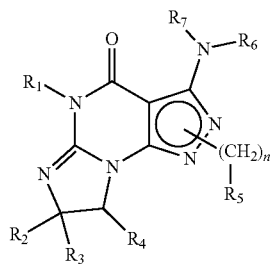

Formula III wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—$CH_3$) and $C_{1-6}$-hydroxyalkyl (e.g., 1-hydroxyethyl);
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and
(vi) n is 1, 2, 3, or 4,
in free or salt form.

In yet another embodiment the invention provides that the PDE1 inhibitors for use in the methods of treatment and prophylaxis described herein are Formula IV

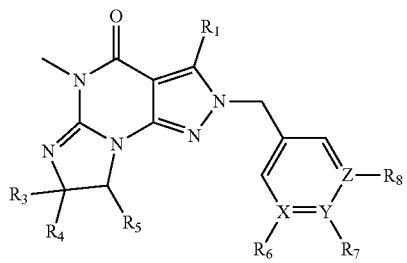

Formula IV in free or salt form, wherein
(i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;
(ii) X, Y and Z are, independently, N or C;
(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively), (iv) $R_6$, $R_7$ and $R_8$ are independently:
H,
$C_{1-4}$alkyl (e.g., methyl),
pyrid-2-yl substituted with hydroxy, or
—S(O)$_2$—NH$_2$;
(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy.

In another embodiment the invention provides that the PDE1 inhibitors for use in the methods as described herein are Formula V:

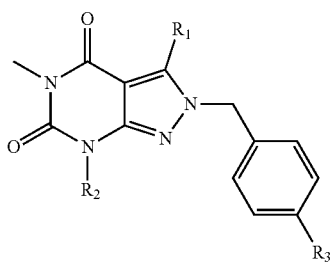

Formula V wherein
(i) $R_1$ is —NH($R_4$), wherein $R_4$ is phenyl optionally substituted with halo (e.g., fluoro), for example, 4-fluorophenyl;
(ii) $R_2$ is H or $C_{1-6}$alkyl (e.g., methyl, isobutyl or neopentyl);
(iii) $R_3$ is —SO$_2$NH$_2$ or —COOH;
in free or salt form.

In another embodiment the invention provides that the PDE1 inhibitors for use in the methods as described herein are Formula VI:

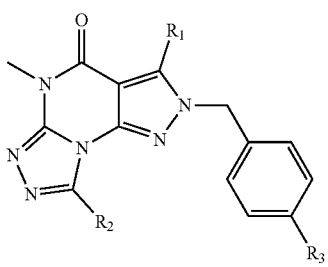

Formula VI wherein
(i) $R_1$ is —NH($R_4$), wherein $R_4$ is phenyl optionally substituted with halo (e.g., fluoro), for example, 4-fluorophenyl;
(ii) $R_2$ is H or $C_{1-6}$alkyl (e.g., methyl or ethyl);
(iii) $R_3$ is H, halogen (e.g., bromo), $C_{1-6}$alkyl (e.g., methyl), aryl optionally substituted with halogen (e.g., 4-fluorophenyl), heteroaryl optionally substituted with halogen (e.g., 6-fluoropyrid-2-yl or pyrid-2-yl), or acyl (e.g., acetyl),
in free or salt form.

In one embodiment, the present disclosure provides for administration of a PDE1 inhibitor for use in the methods described herein (e.g., a compound according to Formulas I, Ia, II, III, IV, V, and/or VI), wherein the inhibitor is a compound according to the following:

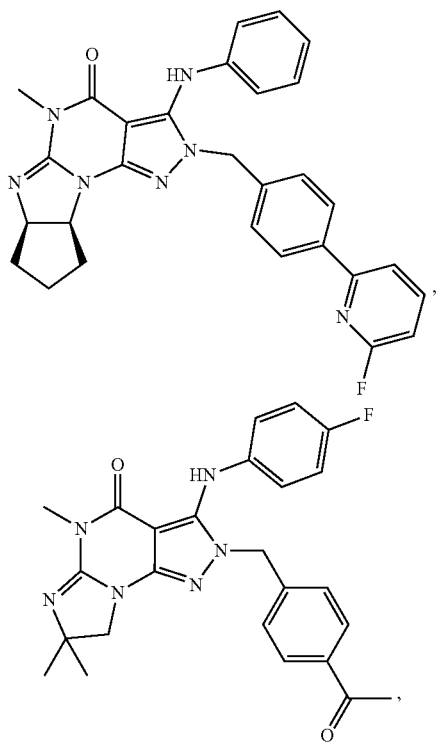
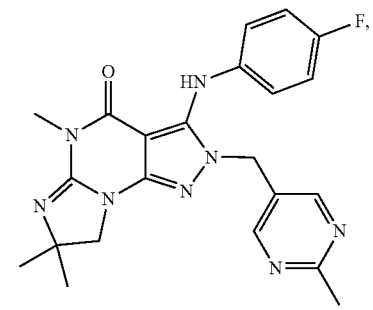
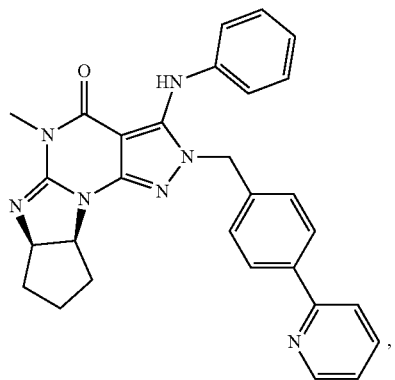
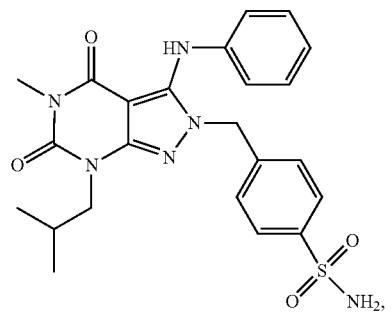
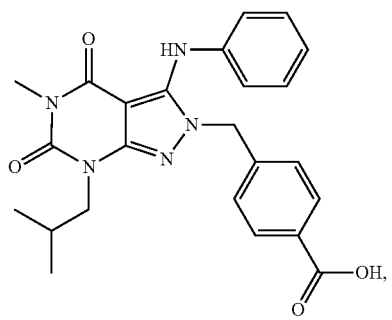
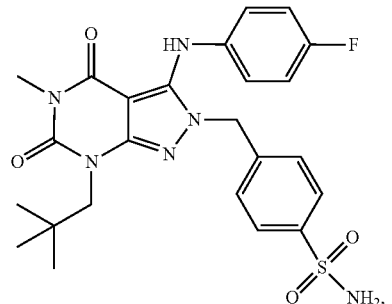
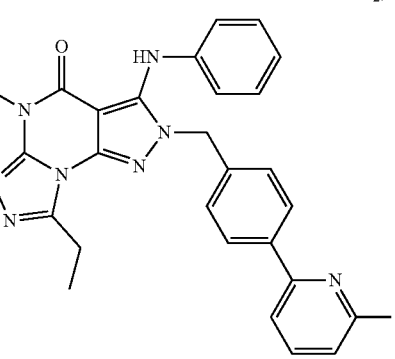
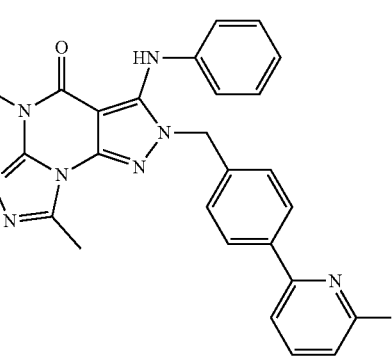

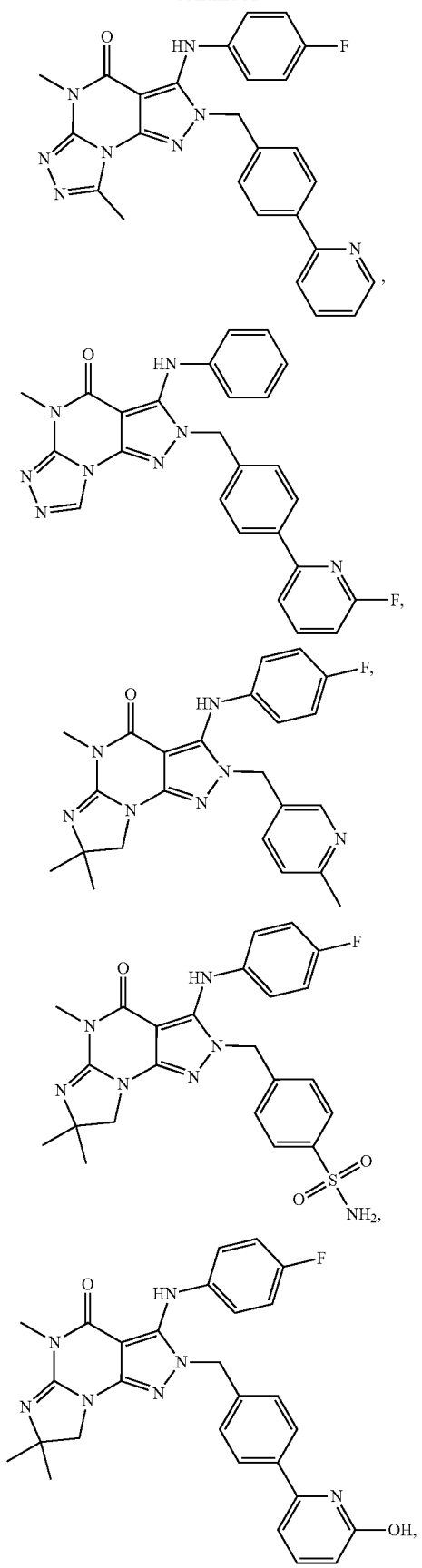
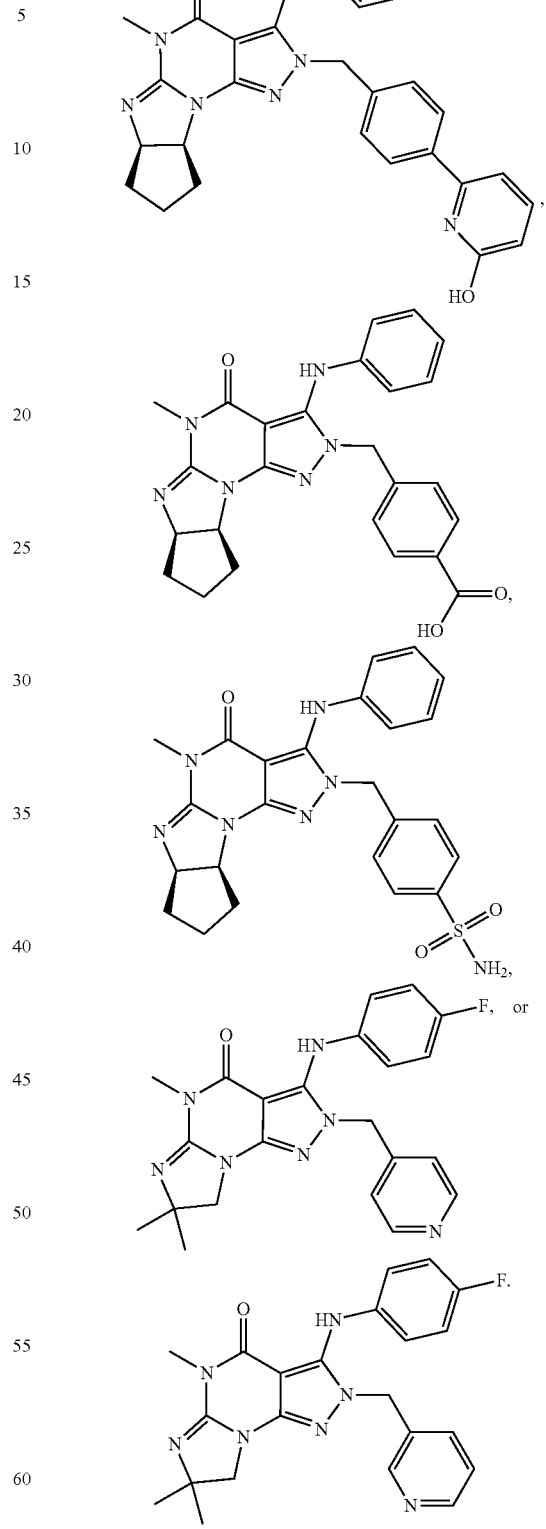
In one embodiment the invention provides administration of a PDE1 inhibitor for use in the methods described herein, wherein the inhibitor is a compound according to the following:

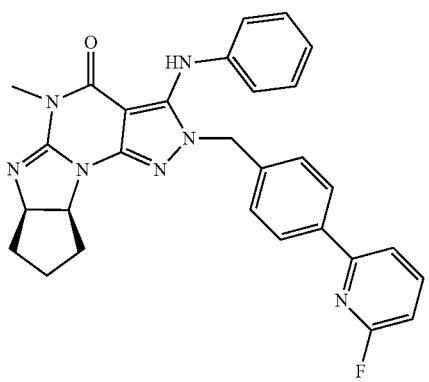 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In another embodiment, the invention provides administration of a PDE1 inhibitor for use in the methods described herein, wherein the inhibitor is a compound according to the following:

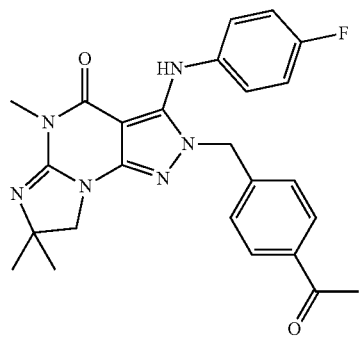 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for use in the methods described herein, wherein the inhibitor is a compound according to the following:

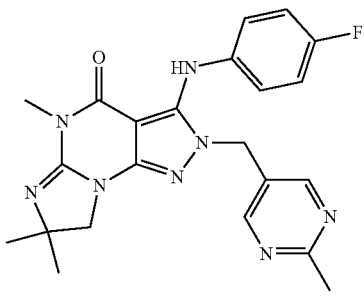 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for use in the methods described herein, wherein the inhibitor is a compound

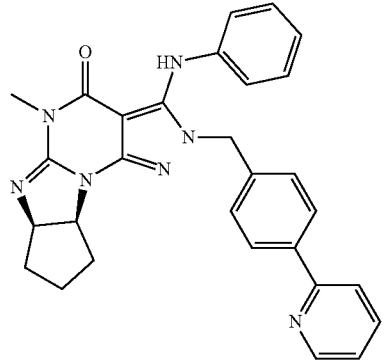 [SMILES: Cn1c(=O)/c(=C(/NCc2ccc(-c3ccccn3)cc2)Nc2ccccc2)c(=N)n2c1=N[C@@H]1CCC[C@@H]12]

in free or pharmaceutically acceptable salt form.

In still another embodiment, the invention provides administration of a PDE1 inhibitor for use in the methods described herein, wherein the inhibitor is a compound according to the following:

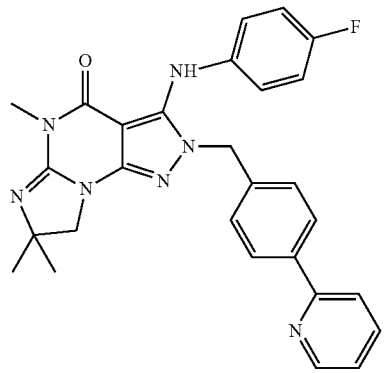 [SMILES: CN1C(=O)c2c(nn(Cc3ccc(-c4ccccn4)cc3)c2Nc2ccc(F)cc2)N2CC(C)(C)N=C12]

in free or pharmaceutically acceptable salt form.

In one embodiment, selective PDE1 inhibitors of any of the preceding formulae (e.g., Formulas I, Ia, II, III, IV, V, and/or VI) are compounds that inhibit phosphodiesterase-mediated (e.g., PDE1-mediated, especially PDE1B-mediated) hydrolysis of cGMP, e.g., the preferred compounds have an IC50 of less than 1 μM, preferably less than 500 nM, preferably less than 50 nM, and preferably less than 5 nM in an immobilized-metal affinity particle reagent PDE assay, in free or salt form.

In other embodiments, the invention provides administration of a PDE1 inhibitor for treatment according to the methods described herein, wherein the inhibitor is a compound according to the following:

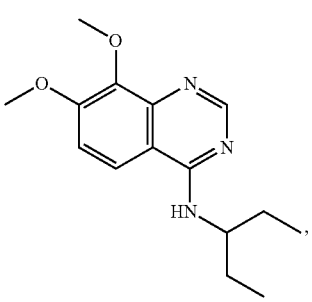

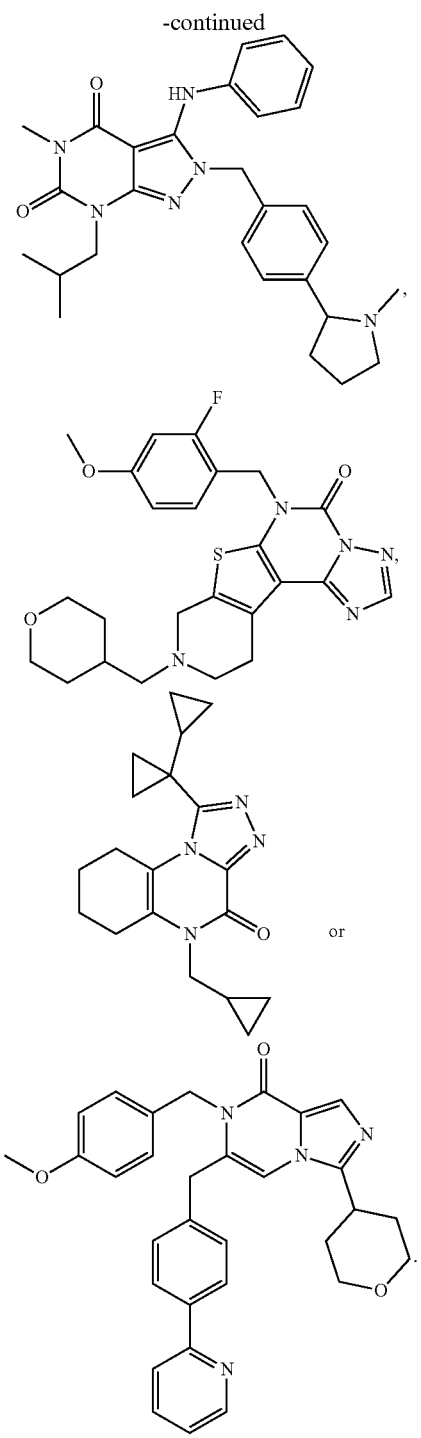

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; U.S. Publication 2017/0291901A1; International Publication WO2018/115067; U.S. Publication 2018/0179200A; U.S. Publication US20160318910A1; U.S. Pat. No. 9,868,741; International Publication WO2017/139186A1; International Application WO2016/040083; U.S. Publication 2017/0240532; International Publication WO2016033776A1; U.S. Publication 2017/0233373; International Publication WO2015130568; International Publication WO2014159012; U.S. Pat. Nos. 9,034,864; 9,266,859; International Publication WO2009085917; U.S. Pat. No. 8,084,261; International Publication WO2018039052; U.S. Publication US20180062729; and International Publication WO2019027783 each of which are incorporated by reference in their entirety. In any situation in which the statements of any documents incorporated by reference contradict or are incompatible with any statements made in the present disclosure, the statements of the present disclosure shall be understood as controlling.

Still further examples of PDE1 inhibitors and suitable methods of use are disclosed in International Application PCT/US2019/033941 and U.S. Provisional Application 62/789,499, both of which are incorporated by reference herein.

In one embodiment, selective PDE1 inhibitors of the any of the preceding formulae (e.g., Formulas I, Ia, II, III, IV, V, and/or VI) are compounds that inhibit phosphodiesterase-mediated (e.g., PDE1-mediated, especially PDE1B-mediated) hydrolysis of cGMP, e.g., the preferred compounds have an $IC_{50}$ of less than 1 M, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

"Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

"Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

"Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

"Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

"Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Invention, e.g., optionally substituted 7,8-dihydro-imidazo[1,2-a]pyrazolo[4,3-e]pyrimidin-4-one compounds and 7,8,9-trihydro-[1H or 2H]-pyrimido [1,2-a]pyrazolo[4,3-e]pyrimidin-4(5H)-one compounds, in free or pharmaceutically acceptable salt form, e.g., Compounds of Formulas I, Ia, II, III, IV, V, and/or VI, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example, when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier, for use as an anti-inflammatory agent.

Methods of Making Compounds of the Invention

Compounds of the Invention may in some cases also exist in prodrug form. A prodrug form is compound which converts in the body to a Compound of the Invention. For example, when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier, for use as an anti-inflammatory agent.

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, and U.S. Pat. No. 9,073,936, the contents of each of which herein are hereby incorporated by reference in their entireties.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}$C, $^{15}$N, is $^{18}$O. Alternatively, unstable isotopes, which are radioactive isotopes which contain additional neutrons compared to the abundant nuclides of the same species (i.e., element), e.g., $^{123}$I, $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Methods of Using Compounds of the Invention

The Compounds of the Invention are useful in the treatment of inflammatory diseases or conditions, particularly inflammatory diseases or conditions. Therefore, administration or use of a preferred PDE1 inhibitor as described herein, e.g., a PDE1 inhibitor as hereinbefore described, e.g., a Compound of Formulas I, Ia, II, III, IV, V, and/or VI provides a means to regulate inflammation (e.g., prevent, reduce, and/or reverse inflammation, and diseases or disorders related to inflammation), and in certain embodiments provide a treatment for various inflammatory diseases and disorders.

In one embodiment, the invention provides a method (Method 1) of treatment or prophylaxis of an inflammatory disease, condition or disorder consequent to a viral infection, the method comprising administering a pharmaceutically effective amount of a specific inhibitor of phosphodiesterase type I (e.g., PDE1 inhibitor, e.g., a PDE1B inhibitor) (e.g., a PDE1 inhibitor of Formulas I, Ia, II, III, IV, V, and/or VI as herein described) to a patient in need thereof.

For example, further embodiments of Method 1 are provided as follows:

1.1. Method 1 wherein the inflammatory condition is mediated by macrophage activation.
1.2. Method 1 or 1.1, wherein the treatment or prophylaxis promotes activation of M2 macrophages.
1.3. Method 1 or 1.1 wherein the viral infection, is a coronavirus infection (e.g., a Severe Acute Respiratory Syndrome Coronavirus (e.g., SARS-CoV, SARS-CoV-2), a Middle East Respiratory Syndrome coronavirus (MERS), 229E coronavirus, NL63 coronavirus, OC43 coronavirus, HKU1 coronavirus).
1.4. Any preceding method wherein the inflammatory disease, condition or disorder is acute respiratory distress syndrome (ARDS).
1.5. Any preceding method wherein the inflammatory disease, condition or disorder is cytokine storm syndrome (CSS).
1.6. Any preceding method wherein the inflammatory disease, condition or disorder is viral sepsis.
1.7. Any preceding method wherein the inflammatory disease, condition or disorder is cytokine storm syndrome (CSS) consequent to infection with SARS-CoV-2.
1.8. Any preceding method wherein the inflammatory disease, condition or disorder is acute respiratory distress syndrome consequent to infection with SARS-CoV-2.
1.9. Any preceding method wherein the inflammatory disease, condition or disorder is viral sepsis consequent to infection with SARS-CoV-2.
1.10. Any preceding method wherein the inflammatory disease, condition or disorder is characterized by elevated IL-6 consequent to infection with SARS-CoV-2.
1.11. Any preceding method wherein the inflammatory disease, condition or disorder is characterized by elevated TNF-α consequent to infection with SARS-CoV-2.
1.12. Any preceding method wherein the inflammatory disease, condition or disorder is characterized by elevated IL-6 consequent to infection with SARS-CoV-2. preceding method wherein the inflammatory condition is characterized by elevated GM-CSF consequent to infection with SARS-CoV-2.
1.13. Any preceding method wherein the inflammatory disease, condition or disorder is characterized by elevated CXCL10, CCL7 and/or IL-1 receptor antagonist consequent to infection with SARS-CoV-2.
1.14. Any preceding method wherein the inflammatory disease, condition or disorder consequent to a viral infection is selected from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, a kidney inflammation-related disorder, or a defined systemic inflammation-related disorder.
1.15. Any preceding method wherein the inflammatory disease, condition or disorder consequent to a viral infection is a gastrointestinal inflammation-related disorder, e.g., selected from colitis, enterocolitis, colitis complicated by intestinal perforation, hepatitis, and pancreatitis.
1.16. Any preceding method wherein the inflammatory disease, condition or disorder consequent to a viral infection is an endocrine inflammation-related disorder, e.g., selected from hypophysitis (e.g., manifested as panhypopitutarism), thyrotoxicosis, hypothyroidism, syndrome of inappropriate secretion of antidiuretic hormone, central adrenal insufficiency, primary adrenal insufficiency, and diabetes mellitus.
1.17. Any preceding method wherein the inflammatory disease, condition or disorder consequent to a viral infection is a dermatologic inflammation-related disorder, e.g., selected from a rash, pruritis, vitiligo, dermatitis, sweet syndrome, drug eruption, poliosis, delayed hypersensitivity reaction, alopecia universalis, grover disease, pyoderma gangrenosum, toxic epidermal necrolysis, chronic non-caseation granuloma, bullous pemphigoid, and psoriasis.

1.18. Any preceding method wherein the inflammatory disease, condition or disorder consequent to a viral infection is an ophthalmologic inflammation-related disorder, e.g., selected from uveitis, conjunctivitis, orbital inflammation, Grave's ophthalmology, choroidal neovascularization, optic neuropathy, keratitis, and retinopathy.

1.19. Any preceding method wherein the inflammatory disease, condition or disorder consequent to a viral infection is a neurologic inflammation-related disorder, e.g., selected from encephalopathy; Guillain-Barre syndrome; polyradiculoneuropathy; symmetrical multifocal neuropathy; transverse myelitis; necrotizing myelopathy; myasthenia gravis; phrenic nerve palsy; immune related meningitis; encephalitis; stroke; meningioradiculoneuritis; peripheral neuropathy; autoimmune inner ear disease; multiple sclerosis; inflammatory enteric neuropathy; mood changes; psychosis; neuromuscular dysfunction; mania; insomnia; suicidality; delirium; narcolepsy; seizures; anosmia; ageusia; obsessive compulsive disorder; neuroinflammation related to neurodegenerative conditions such as Alzheimer's disease (AD), Parkinson's disease (PD), amyotrophic lateral sclerosis (ALS); demyelination consequent to multiple sclerosis (MS), prion diseases, stroke, cardiac arrest, hypoxia, intracerebral hemorrhage or traumatic brain injury; conditions characterized by abnormal neurotransmitter production and/or response, including depression, schizophrenia, post-traumatic stress disorder, pain disorder, panic disorder, anxiety, attention deficit disorder, bipolar disease; e.g., wherein any of the foregoing are associated with neuroinflammation, chronic CNS infections, including Lyme disease, CNS infection consequent to an immunosuppressive condition, HIV-dementia; or neuroinflammation consequent to chemotherapy.

1.20. Any preceding method wherein the inflammatory disease, condition or disorder consequent to a viral infection is a hematologic inflammation-related disorder, e.g., selected from thrombocytopenia, pancytopenia, neutropenia, lymphopenia, coagulopathy, hyperferritinemia, hemorrhagic rash, hypofibrinogenemia, hemophagocytosis, eosinophilia, pure red blood cell aplasia, acquired hemophilia A, disseminated intravascular coagulopathy, stroke, embolism (e.g., pulmonary embolism), ischemia, and hypoxia.

1.21. Any preceding method wherein the inflammatory disease, condition or disorder consequent to a viral infection is a genitourinary inflammation-related disorder, e.g., selected from renal failure, acute/granulomatous interstitial nephritis, acute tubular necrosis, and lymphotic vasculitis (e.g., lymphotic vasculitis of the uterus).

1.22. Any preceding method wherein the inflammatory disease, condition or disorder consequent to a viral infection is a respiratory inflammation-related disorder, e.g., selected from dyspnea, pneumonitis, pneumonia, acute respiratory distress syndrome, asthma, chronic obstructive pulmonary disease, pulmonary fibrosis, and allergic rhinitis.

1.23. Any preceding method wherein the inflammatory disease, condition or disorder consequent to a viral infection is a musculoskeletal inflammation-related disorder, e.g., selected from polyarthritis, juvenile idiopathic arthritis, athralgia, myalgia, chronic granulomatous inflammation of rectus abdominis muscle, and rhabdomyolysis.

1.24. Any preceding method wherein the inflammatory disease, condition or disorder consequent to a viral infection is a cardiac inflammation-related disorder, e.g., selected from precarditis, takotsubo like syndrome, endocarditis, myocarditis, cardiomyopathy, arrhythmias, acute cardiac injury, and cardiogenic shock.

1.25. Any preceding method wherein the inflammatory disease, condition or disorder consequent to a viral infection is a kidney inflammation-related disorder, e.g., selected from glomerulonephritis (e.g., membranoproliferative glomerulonephritis), interstitial nephritis, IgA nephropathy (i.e., Berger's Disease), pyelonephritis, chronic kidney disease, kidney failure, lupus nephritis, Goodpasture's syndrome, Wegener's granulomatosis, 1.26. Any preceding method wherein the inflammatory disease, condition or disorder consequent to a viral infection is a systemic inflammation-related disorder, e.g. selected from macrophage activation syndrome (MAS), lung sarcoidosis, cutaneous and pulmonary sarcoidosis, polymyalgia rheumatica, Still's Disease, hepatosplenomegaly, lymphadenopathy, liver disease, systemic lupus erythematosus, hypertriglyceridemia, giant cell arteritis, muscular sarcoidosis, neurological and pulmonary sarcoidosis, celiac disease, lupus nephritis, dermamyositis, autoimmune inflammatory myopathy, Vogt-Koyanagi like syndrome, multisystem inflammatory disease, Kawasaki disease, secondary hemophagocytic lymphohistiocytosis, and cytokine release syndrome.

1.27. Any preceding method, wherein the inflammatory disease, condition or disorder consequent to a viral infection is macrophage activation syndrome (MAS).

1.28. Any preceding method, wherein the inflammatory disease, condition or disorder consequent to a viral infection is a hemophagocytic lymphohistiocytosis.

1.29. Any preceding method, wherein the inflammatory disease, condition or disorder consequent to a viral infection is secondary hemophagocytic lymphohistiocytosis. Any preceding method, wherein the inflammatory disease, condition or disorder consequent to a viral infection is Kawasaki disease.

1.30. Any preceding method, wherein the patient is at risk for developing an inflammatory disease, disorder or condition consequent to a viral infection, e.g., wherein the patient is diabetic, obese, elderly, or suffers from hypertension.

1.31. Any preceding method, wherein the patient exhibits one or more symptoms of a viral infection (e.g., infection of a coronavirus, e.g., infection of SARS-CoV-2), e.g., one or more of fever, aches, tiredness, sore throat, cough, shortness of breath, and respiratory distress.

1.32. Any foregoing method comprising administering an effective amount of a PDE1 inhibitor of the current invention (e.g., a PDE1 inhibitor of Formulas I, Ia, II, III, IV, V, and/or VI as herein described) in an amount effective to (i) reduce or inhibit activation of M1 macrophages, and/or (ii) an amount effective to reduce levels of one or more pro-inflammatory cytokines (e.g., IL-1β, TNF-α, IL-6 and Ccl2, or combination thereof); and/or (iii) an amount effective to reduce T-cell exhaustion; and/or (iv) an amount effective to inhibit recruitment of immune cells, e.g., macrophages and/or microglia, e.g., chemokine-mediated recruitment, e.g., Ccl2-mediated recruitment, to an inflammatory site; to a patient in need thereof.

1.33. Any foregoing method comprising administering an effective amount of a PDE1 inhibitor of the current invention (e.g., a PDE1 inhibitor of Formulas I, Ia, II, III, IV, V, and/or VI as herein described) to a patient in need thereof, in an amount effective to (i) promote activation of M2 macrophages, and/or (ii) an amount effective to promote anti-inflammatory cytokines (e.g., IL-10) relative to pro-inflammatory cytokines (e.g., IL-6), and/or (iii) an amount effective to normalize lymphocyte counts in a patient in need thereof.

1.34. Any foregoing method comprising administering an effective amount of a PDE1 inhibitor of the current invention (e.g., a PDE1 inhibitor of Formulas I, Ia, II, III, IV, V, and/or VI as herein described) to a patient in need thereof, in an amount effective to reduce levels of macrophages of the M1 phenotype and/or enhance levels of macrophages of the M2 phenotype.

1.35. Any foregoing method wherein the inflammation is associated with increased expression and/or activation of macrophages (e.g., M1 macrophages).

1.36. Any foregoing method wherein the PDE1 inhibitor blunts or inhibits the expression and/or activity of pro-inflammatory cytokines, e.g., selected from the group consisting of: IL-1B, IL-6, TNF-α, Ccl2, Nitric Oxide (NO), and Reactive Oxygen Species (ROS).

1.37. Any foregoing method wherein the PDE1 inhibitor in administered in combination with a PDE4 inhibitor (e.g., rolipram).

1.38. Any foregoing method wherein the patient exhibits increased levels of pro-inflammatory cytokines (e.g., IL-1B, IL-6, TNF-alpha, Ccl2).

1.39. Any foregoing method wherein "PDE1 inhibitor" describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

1.40. Any foregoing method wherein the PDE1 inhibitor inhibits the activity of PDE1 (e.g., bovine PDE1 in the assay described in Example 1) with an $IC_{50}$ of less than 10 nM, e.g., wherein the PDE1 inhibitor does not inhibit the activity of PDE types other than PDE1, e.g., has an $IC_{50}$ at least 1000 times greater for PDE types other than PDE1.

1.41. Any foregoing method wherein the PDE1 inhibitor is a Compound of Formulas I, Ia, II, III, IV, V, and/or VI.

1.42. Any foregoing method, wherein the PDE1 inhibitor is the following:

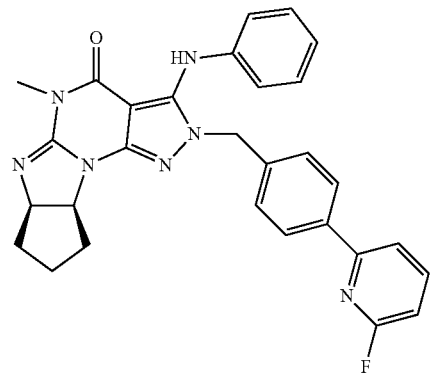 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable form.

1.43. Any foregoing method, wherein the PDE1 inhibitor is the following:

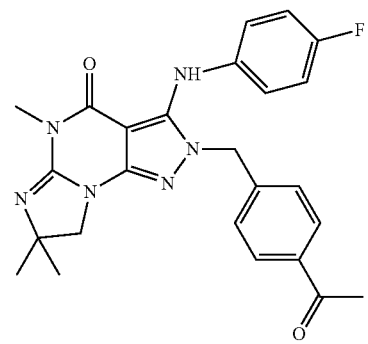 [SMILES: CC(=O)c1ccc(Cn2nc3c(c2Nc2ccc(F)cc2)C(=O)N(C)C2=NC(C)(C)CN23)cc1]

in free or pharmaceutically acceptable form.

1.44. Any foregoing method, wherein the PDE1 inhibitor is the following:

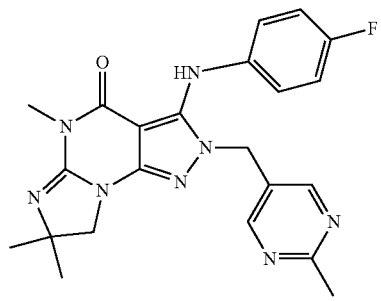 [SMILES: Cc1ncc(Cn2nc3c(c2Nc2ccc(F)cc2)C(=O)N(C)C2=NC(C)(C)CN23)cn1]

in free or pharmaceutically acceptable form.

1.45. Any foregoing method, wherein the PDE1 inhibitor is the following:

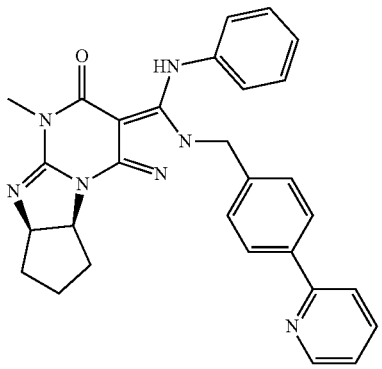 [SMILES: Cn1c(=O)/c(=C(/NCc2ccc(-c3ccccn3)cc2)Nc2ccccc2)c(=N)n2c1=N[C@@H]1CCC[C@@H]12]

in free or pharmaceutically acceptable form.
1.46. Any of the foregoing method wherein the patient has elevated levels of one or more pro-inflammatory cytokines (e.g., selected from IL1β, TNFα, Ccl2, IL-6, and combinations thereof).
1.47. Any of the foregoing method wherein the patient has reduced levels of one or more anti-inflammatory cytokines (e.g., IL-10).
1.48. Any of the foregoing method wherein the patient has elevated levels of macrophages of the M1 phenotype compared to macrophages of the M2 phenotype.
1.49. Any of the foregoing methods wherein the patient is also administered one or more of an antibiotic agent, antiviral agent, a corticosteroid and/or an NSAID.
1.50. Any of the foregoing methods wherein the patient is also administered an antiviral agent.
1.51. Any of the foregoing methods wherein the patient is also administered a monoclonal antibody that blocks or inhibits an inflammatory cytokine or inflammatory cytokine receptor.
1.52. Any preceding method comprising coadministration with remdesivir.
1.53. Any preceding method comprising coadministration with EIDD-2801.
1.54. Any preceding method comprising coadministration with favipiravir.
1.55. Any preceding method comprising coadministration with tocilizumab,
1.56. Any preceding method comprising coadministration with camostat or pharmaceutically acceptable salt thereof, e.g., camostat mesylate.
1.57. Any preceding method comprising coadministration with ivermectin.
1.58. Any preceding method comprising coadministration with duvelisib.
1.59. Any preceding method comprising coadministration with deferoxamine.
1.60. Any preceding method comprising coadministration with canakinumab.
1.61. Any preceding method comprising coadministration with lopinavir and/or ritonavir.
1.62. Any preceding method comprising coadministration with acalabrutinib.
1.63. Any preceding method comprising coadministration with baricitinib
1.64. Any preceding method comprising coadministration with bemcentinib
1.65. Any preceding method comprising coadministration with bevacizumab.
1.66. Any preceding method comprising coadministration with leronlimab.
1.67. Any preceding method comprising coadministration with sarilumab.
1.68. Any preceding method comprising coadministration with umifenovir.
1.69. Any preceding method comprising coadministration with anakinra.
1.70. Any preceding method comprising coadministration with emapalumab.
1.71. Any preceding method comprising coadministration with inhaled nitric oxide (NO).
1.72. Any preceding method comprising coadministration with a nitric oxide (NO) donor, e.g., selected from Diethylene glycol dinitrate, Glyceryl trinitrate (nitroglycerin), Isosorbide mononitrate and dinitrate, Itramin tosilate, Nicorandil, Pentaerithrityl tetranitrate, Propatylnitrate, Sinitrodil, Tenitramine, Trolnitrate, and sodium nitroprusside.
1.73. Any preceding method comprising coadministration with a PDE V inhibitor, e.g., selected from sildenafil, tadalafil, vardenafil and avanafil.
1.74. Any foregoing method wherein the pharmaceutically effective amount of the specific inhibitor of phosphodiesterase type I is an oral daily dosage of 1-20 mg.

The invention further provides the use of a PDE1 inhibitor, e.g., any of a Compound of Formulas I, Ia, II, III, IV, V, and/or VI in the manufacture of a medicament for use in any of Methods 1, et seq.

The invention further provides a PDE1 inhibitor, e.g., any of a Compound of Formulas I, Ia, II, III, IV, V, and/or VI for use in any of Methods 1, et seq.

The invention further provides a pharmaceutical composition comprising a PDE1 inhibitor, e.g., any of a Formulas I, Ia, II, III, IV, V, and/or VI for use in any of Methods 1 et seq.

In further aspects, the present invention is directed to a method [Method 2] of (i) promoting macrophage activation to the M2 activation state and/or (ii) inhibiting the recruitment of macrophages and/or microglia, e.g., chemokine-mediated recruitment, e.g., Ccl2-mediated recruitment, to an inflammatory site in a patient suffering from a viral infection or an inflammatory disease, condition or disorder consequent to a viral infection, the method comprising administering a pharmaceutically effective amount of a specific inhibitor of phosphodiesterase type I (e.g., PDE1 inhibitor, e.g., a PDE1B inhibitor) (e.g., a PDE1 inhibitor of Formulas I, Ia, II, III, IV, V, and/or VI as herein described) to the patient.

For example, further embodiments of Method 1 are provided as follows:
2.1 Method 2, wherein the patient is suffering from a viral infection, e.g. a coronavirus infection (e.g., an infection of a Severe Acute Respiratory Syndrome Coronavirus (e.g., SARS-CoV, SARS-CoV-2), a Middle East Respiratory Syndrome coronavirus (MERS), 229E coronavirus, NL63 coronavirus, OC43 coronavirus, HKU1 coronavirus).
2.2 Any preceding method wherein the inflammatory disease, condition or disorder is acute respiratory distress syndrome (ARDS).
2.3 Any preceding method wherein the inflammatory disease, condition or disorder is cytokine storm syndrome (CSS).

2.4 Any preceding method wherein the inflammatory disease, condition or disorder is viral sepsis.

2.5 Any preceding method wherein the inflammatory disease, condition or disorder is cytokine storm syndrome (CSS) consequent to infection with SARS-CoV-2.

2.6 Any preceding method wherein the inflammatory disease, condition or disorder is acute respiratory distress syndrome consequent to infection with SARS-CoV-2.

2.7 Any preceding method wherein the inflammatory disease, condition or disorder is viral sepsis consequent to infection with SARS-CoV-2.

2.8 Any preceding method wherein the inflammatory disease, condition or disorder is characterized by elevated IL-6 consequent to infection with SARS-CoV-2.

2.9 Any preceding method wherein the inflammatory disease, condition or disorder is characterized by elevated TNF-α consequent to infection with SARS-CoV-2.

2.10 Any preceding method wherein the inflammatory disease, condition or disorder is characterized by elevated IL-6 consequent to infection with SARS-CoV-2. preceding method wherein the inflammatory condition is characterized by elevated GM-CSF consequent to infection with SARS-CoV-2.

2.11 Any preceding method wherein the inflammatory disease, condition or disorder is characterized by elevated CXCL10, CCL7 and/or IL-1 receptor antagonist consequent to infection with SARS-CoV-2.

2.12 Any preceding method, wherein the subject is suffering from an inflammatory disease, condition or disorder consequent to a viral infection.

2.13 Any preceding method wherein the inflammatory disease, condition or disorder consequent to a viral infection is selected from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, a kidney inflammation-related disorder, or a defined systemic inflammation-related disorder.

2.14 Any preceding method wherein the inflammatory disease, condition or disorder consequent to a viral infection is a gastrointestinal inflammation-related disorder, e.g., selected from colitis, enterocolitis, colitis complicated by intestinal perforation, hepatitis, and pancreatitis.

2.15 Any preceding method wherein the inflammatory disease, condition or disorder consequent to a viral infection is an endocrine inflammation-related disorder, e.g., selected from hypophysitis (e.g., manifested as panhypopitutarism), thyrotoxicosis, hypothyroidism, syndrome of inappropriate secretion of antidiuretic hormone, central adrenal insufficiency, primary adrenal insufficiency, and diabetes mellitus.

2.16 Any preceding method wherein the inflammatory disease, condition or disorder consequent to a viral infection is a dermatologic inflammation-related disorder, e.g., selected from a rash, pruritis, vitiligo, dermatitis, sweet syndrome, drug eruption, poliosis, delayed hypersensitivity reaction, alopecia universalis, grover disease, pyoderma gangrenosum, toxic epidermal necrolysis, chronic non-caseation granuloma, bullous pemphigoid, and psoriasis.

2.17 Any preceding method wherein the inflammatory disease, condition or disorder consequent to a viral infection is an ophthalmologic inflammation-related disorder, e.g., selected from uveitis, conjunctivitis, orbital inflammation, Grave's ophthalmology, choroidal neovascularization, optic neuropathy, keratitis, and retinopathy.

2.18 Any preceding method wherein the inflammatory disease, condition or disorder consequent to a viral infection is a neurologic inflammation-related disorder, e.g., selected from encephalopathy, Guillain-Barre syndrome, polyradiculoneuropathy, symmetrical multifocal neuropathy, transverse myelitis, necrotizing myelopathy, myasthenia gravis, phrenic nerve palsy, immune related meningitis, encephalitis, stroke, meningioradiculoneuritis, peripheral neuropathy, autoimmune inner ear disease, multiple sclerosis, inflammatory enteric neuropathy, mood changes; psychosis; neuromuscular dysfunction; mania; insomnia; suicidality; delirium; narcolepsy; seizures; anosmia; ageusia; obsessive compulsive disorder; neuroinflammation related to neurodegenerative conditions such as Alzheimer's disease (AD), Parkinson's disease (PD), amyotrophic lateral sclerosis (ALS); demyelination consequent to multiple sclerosis (MS), prion diseases, stroke, cardiac arrest, hypoxia, intracerebral hemorrhage or traumatic brain injury; conditions characterized by abnormal neurotransmitter production and/or response, including depression, schizophrenia, post-traumatic stress disorder, pain disorder, panic disorder, anxiety, attention deficit disorder, bipolar disease, e.g., wherein any of the foregoing are associated with neuroinflammation, chronic CNS infections, including Lyme disease, CNS infection consequent to an immunosuppressive condition, HIV-dementia; or neuroinflammation consequent to chemotherapy.

2.19 Any preceding method wherein the inflammatory disease, condition or disorder consequent to a viral infection is a hematologic inflammation-related disorder, e.g., selected from thrombocytopenia, pancytopenia, neutropenia, lymphopenia, coagulopathy, hyperferritinemia, hemorrhagic rash, hypofibrinogenemia, hemophagocytosis, eosinophilia, pure red blood cell aplasia, acquired hemophilia A, disseminated intravascular coagulopathy, stroke, embolism (e.g., pulmonary embolism), ischemia, and hypoxia.

2.20 Any preceding method wherein the inflammatory disease, condition or disorder consequent to a viral infection is a genitourinary inflammation-related disorder, e.g., selected from renal failure, acute/granulomatous interstitial nephritis, acute tubular necrosis, and lymphotic vasculitis (e.g., lymphotic vasculitis of the uterus).

2.21 Any preceding method wherein the inflammatory disease, condition or disorder consequent to a viral infection is a respiratory inflammation-related disorder, e.g., selected from dyspnea, pneumonitis, pneumonia, acute respiratory distress syndrome, asthma, chronic obstructive pulmonary disease, pulmonary fibrosis, and allergic rhinitis.

2.22 Any preceding method wherein the inflammatory disease, condition or disorder consequent to a viral infection is a musculoskeletal inflammation-related disorder, e.g., selected from polyarthritis, athralgia, juvenile idiopathic arthritis, myalgia, chronic granulomatous inflammation of rectus abdominis muscle, and rhabdomyolysis.

2.23 Any preceding method wherein the inflammatory disease, condition or disorder consequent to a viral infection is a cardiac inflammation-related disorder, e.g., selected from precarditis, takotsubo like syndrome, endocarditis, myocarditis, cardiomyopathy, arrhythmias, acute cardiac injury, and cardiogenic shock.

2.24 Any preceding method wherein the inflammatory disease, condition or disorder consequent to a viral infection is a kidney inflammation-related disorder, e.g., selected from glomerulonephritis (e.g., membranoproliferative glomerulonephritis), interstitial nephritis, IgA nephropathy (i.e., Berger's Disease), pyelonephritis, chronic kidney disease, kidney failure, lupus nephritis, Goodpasture's syndrome, Wegener's granulomatosis, 2.25 Any preceding method wherein the inflammatory disease, condition or disorder consequent to a viral infection is a systemic inflammation-related disorder, e.g. selected from macrophage activation syndrome (MAS), lung sarcoidosis, cutaneous and pulmonary sarcoidosis, polymyalgia rheumatica, Still's Disease, hepatosplenomegaly, lymphadenopathy, liver disease, systemic lupus erythematosus, hypertriglyceridemia, giant cell arteritis, muscular sarcoidosis, neurological and pulmonary sarcoidosis, celiac disease, lupus nephritis, dermamyositis, autoimmune inflammatory myopathy, Vogt-Koyanagi like syndrome, multisystem inflammatory disease, Kawasaki disease, secondary hemophagocytic lymphohistiocytosis, and cytokine release syndrome.

2.26 Any preceding method, wherein the inflammatory disease, condition or disorder consequent to a viral infection is macrophage activation syndrome (MAS).

2.27 Any preceding method, wherein the inflammatory disease, condition or disorder consequent to a viral infection is a hemophagocytic lymphohistiocytosis.

2.28 Any preceding method, wherein the inflammatory disease, condition or disorder consequent to a viral infection is secondary hemophagocytic lymphohistiocytosis. Any preceding method, wherein the inflammatory disease, condition or disorder consequent to a viral infection is Kawasaki disease.

2.29 Any preceding method, wherein the patient is at risk for developing an inflammatory disease, disorder or condition consequent to a viral infection, e.g., wherein the patient is diabetic, obese, elderly, or suffers from hypertension.

2.30 Any preceding method, wherein the patient exhibits one or more symptoms of a viral infection (e.g., infection of a coronavirus, e.g., infection of SARS-CoV-2), e.g., one or more of fever, aches, tiredness, sore throat, cough, shortness of breath, and respiratory distress.

2.31 Any foregoing method comprising administering an effective amount of a PDE1 inhibitor of the current invention (e.g., a PDE1 inhibitor of Formulas I, Ia, II, III, IV, V, and/or VI as herein described) in an amount effective to (i) reduce or inhibit activation of M1 macrophages, and/or (ii) an amount effective to reduce levels of one or more pro-inflammatory cytokines (e.g., IL1β, TNF-α, IL6 and Ccl2, or combination thereof); and/or (iii) an amount effective to reduce T-cell exhaustion; and/or (iii) an amount effective to reduce T-cell exhaustion; and/or (iv) an amount effective to inhibit recruitment of immune cells, e.g., macrophages and/or microglia, e.g., chemokine-mediated recruitment, e.g., Ccl2-mediated recruitment, to an inflammatory site; to a patient in need thereof.

2.32 Any foregoing method comprising administering an effective amount of a PDE1 inhibitor of the current invention (e.g., a PDE1 inhibitor of Formulas I, Ia, II, III, IV, V, and/or VI as herein described) to a patient in need thereof, in an amount effective to (i) promote activation of M2 macrophages, and/or (ii) an amount effective to promote anti-inflammatory cytokines (e.g., IL-10) relative to pro-inflammatory cytokines (e.g., IL-6); and/or (iii) an amount effective to normalize lymphocyte counts in a patient in need thereof.

2.33 Any foregoing method comprising administering an effective amount of a PDE1 inhibitor of the current invention (e.g., a PDE1 inhibitor of Formulas I, Ia, II, III, IV, V, and/or VI as herein described) to a patient in need thereof, in an amount effective to reduce levels of macrophages of the M1 phenotype and/or enhance levels of macrophages of the M2 phenotype.

2.34 Any foregoing method wherein the inflammation is associated with increased expression and/or activation of macrophages (e.g., M1 macrophages).

2.35 Any foregoing method wherein the PDE1 inhibitor blunts or inhibits the expression and/or activity of pro-inflammatory cytokines, e.g., selected from the group consisting of: IL1B, IL-6, TNF-α, Ccl2, Nitric Oxide (NO), and Reactive Oxygen Species (ROS).

2.36 Any foregoing method wherein the PDE1 inhibitor in administered in combination with a PDE4 inhibitor (e.g., rolipram).

2.37 Any foregoing method wherein the patient exhibits increased levels of pro-inflammatory cytokines (e.g., IL1B, IL6, TNF-alpha, Ccl2).

2.38 Any foregoing method wherein "PDE1 inhibitor" describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

2.39 Any foregoing method wherein the PDE1 inhibitor inhibits the activity of PDE1 (e.g., bovine PDE1 in the assay described in Example 1) with an $IC_{50}$ of less than 10 nM, e.g., wherein the PDE1 inhibitor does not inhibit the activity of PDE types other than PDE1, e.g., has an $IC_{50}$ at least 1000 times greater for PDE types other than PDE1.

2.40 Any foregoing method wherein the PDE1 inhibitor is a Compound of Formulas I, Ia, II, III, IV, V, and/or VI.

2.41 Any foregoing method, wherein the PDE1 inhibitor is the following:

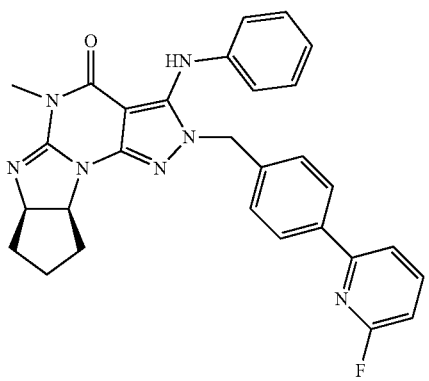 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable form.

2.42 Any foregoing method, wherein the PDE1 inhibitor is the following:

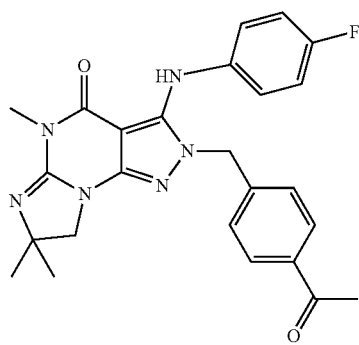 [SMILES: CC(=O)c1ccc(Cn2nc3c(c2Nc2ccc(F)cc2)C(=O)N(C)C2=NC(C)(C)CN23)cc1]

in free or pharmaceutically acceptable form.

2.43 Any foregoing method, wherein the PDE1 inhibitor is the following:

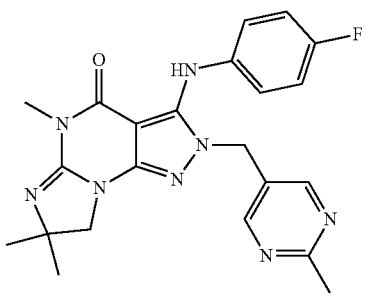 [SMILES: Cc1ncc(Cn2nc3c(c2Nc2ccc(F)cc2)C(=O)N(C)C2=NC(C)(C)CN23)cn1]

in free or pharmaceutically acceptable form.

2.44 Any foregoing method, wherein the PDE1 inhibitor is the following:

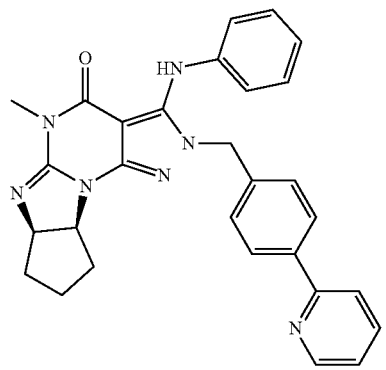 [SMILES: Cn1c(=O)/c(=C(/NCc2ccc(-c3ccccn3)cc2)Nc2ccccc2)c(=N)n2c1=N[C@@H]1CCC[C@@H]12]

in free or pharmaceutically acceptable form.

2.45 Any of the foregoing method wherein the patient has elevated levels of one or more pro-inflammatory cytokines (e.g., selected from IL1β, TNFα, Ccl2, IL-6, and combinations thereof).

2.46 Any of the foregoing method wherein the patient has reduced levels of one or more anti-inflammatory cytokines (e.g., IL-10).

2.47 Any of the foregoing method wherein the patient has elevated levels of macrophages of the M1 phenotype compared to macrophages of the M2 phenotype.

2.48 Any of the foregoing methods wherein the patient is also administered one or more of an antibiotic agent, antiviral agent, corticosteroids or NSAIDs.

2.49 Any foregoing method in conjunction with any method according to Method 1, et seq.

The invention further provides the use of a PDE1 inhibitor, e.g., any of a Compound of Formulas I, Ia, II, III, IV, V, and/or VI in the manufacture of a medicament for use in any of Methods 2, et seq.

The invention further provides a PDE1 inhibitor, e.g., any of a Compound of Formulas I, Ia, II, III, IV, V, and/or VI for use in any of Methods 2, et seq.

The invention further provides a pharmaceutical composition comprising a PDE1 inhibitor, e.g., any of a Formulas I, Ia, II, III, IV, V, and/or VI for use in any of Methods 2, et seq.

The phrase "Compounds of the Invention" or "PDE1 inhibitors of the Invention", or like terms, encompasses any and all of the compounds disclosed herewith, e.g., a Compound of Formulas I, Ia, II, III, IV, V, and/or VI.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat or mitigate a specific disease or disorder, and/or a symptom thereof, and/or to reduce inflammatory cytokines, e.g., as produced by macrophages, and/or to reduce M1 macrophage activation, and/or to increase anti-inflammatory cytokines, e.g., as produced by macrophages, and/or to enhance M2 macrophage activation.

The term "patient" includes a human or non-human (i.e., animal) patient. In a particular embodiment, the invention encompasses both humans and nonhuman animals. In another embodiment, the invention encompasses nonhuman animals. In other embodiments, the term encompasses humans.

The term "comprising" as used in this disclosure is intended to be open-ended and does not exclude additional, unrecited elements or method steps.

The term "T-cell exhaustion" or "exhausted T-cells" refers to a state of T cell dysfunction that arises during many chronic infections and cancer. It is defined by poor effector function, sustained expression of inhibitory receptors, and a transcriptional state distinct from that of functional effector or memory T cells.

Compounds of the Invention, e.g., Formulas I, Ia, II, III, IV, V, and/or VI as hereinbefore described, in free or pharmaceutically acceptable salt form, may be used as a sole therapeutic agent, but may also be used in combination or for co-administration with other active agents.

For example, in certain embodiments, the Compounds of the Invention, e.g., Formulas I, Ia, II, III, IV, V, and/or VI as hereinbefore described, in free or pharmaceutically acceptable salt form, may be administered in combination (e.g. administered sequentially or simultaneously or within a 24 hour period) with other active agents, e.g., with one or more antidepressant agents, e.g., with one or more compounds in free or pharmaceutically acceptable salt form, selected from selective serotonin reuptake inhibitors (SSRIs), serotonin-norepinephrine reuptake inhibitors (SNRIs), c) tricyclic antidepressants (TCAs), and atypical antipsychotics.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg (depending on the drug to be administered and the condition to be treated, for example in the case of Compound 214, 0.5 to 25 mg, e.g., 1 to 10 mg, per diem, e.g., in monophosphate salt form, for treatment of inflammatory conditions), conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg (e.g., 1, 2.5, 5, 10, or 20 mg) of a Compound of the Invention, e.g., together with a pharmaceutically acceptable diluent or carrier therefor.

Pharmaceutical compositions comprising Compounds of the Invention may be prepared using conventional diluents or excipients and techniques known in the galenic art. Thus, oral dosage forms may include tablets, capsules, solutions, suspensions and the like.

EXAMPLES

Example 1: Peripheral Inflammation Assessment Using Mouse Zymosan Pleurisy Model Zymosan is injected into the pleural cavities of mice in order to induce sterile inflammation. Infiltration of leukocytes, neutrophils, and macrophages are monitored at days 3 and 7 following injection. Detection of various cell types are identified according to the gating strategy outlined in Table 1 below.

TABLE 1

Cell types and identifiable markers for flow cytometry

| Cell Type | Expressed Markers |
| --- | --- |
| Leukocytes | CD45+ |
| Neutrophils | CD45+/Ly6G+ |
| Macrophages | CD45+/Ly6G−/CD19−/CD11c−/CD11b+/F4/80+ |
| M1 Macrophages | CD45+/Ly6G−/CD19−/CD11c−/CD11b+/F4/80+CD38+ |
| M2 Macrophages | CD45+/Ly6G−/CD19−/CD11c−/CD11b+/F4/80+/EGR2+ |

In this model, injection of zymosan causes the recruitment of various waves of leukocytes, which are observed and recorded. Exudate volume increases to a maximum over a period of 24 hours, and neutrophils increase within 4 hours and reach a maximum by 48 hours. Lymphocytes of the adaptive immune system enter at a later stage, after three days, which is signaled by macrophages presenting antigens. A resolution phase is well documented in this model and is accompanied by decreased total macrophage number and transition into M2 phenotype.

In the studies, Compounds 1 and 2 were administered to the test subjects, and the effect the compounds had on infiltration of leukocytes, neutrophils, and macrophages was observed.

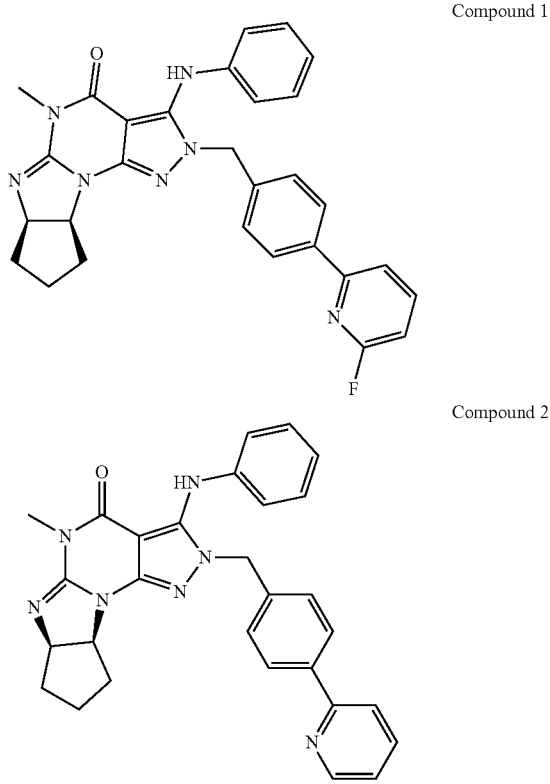

Compound 1

Compound 2

As shown in the accompanying FIGS. 1-9, it was observed that the subjects treated with Compound 1 or 2 showed enhanced inflammatory resolution by promoting shift from M1 to M2. The data show that in the treated specimens, inflammation due to M1 macrophages was consistently decreased, while M2 activation was promoted. As shown in FIG. 1, 1 mg of Zymosan i.p. injection into the peritoneal cavity resulted in significant total CD45+ leukocyte infiltration. This increased total number of leukocytes resulted in a general increase in total macrophage numbers on day 3 and 7 following Zymosan injection in disease only animals compared to naïve (FIG. 2A). The percentage of the macrophages based on the total number of leukocytes (FIG. 2B) slightly decreased between days 3 and 7.

Figure 3A:
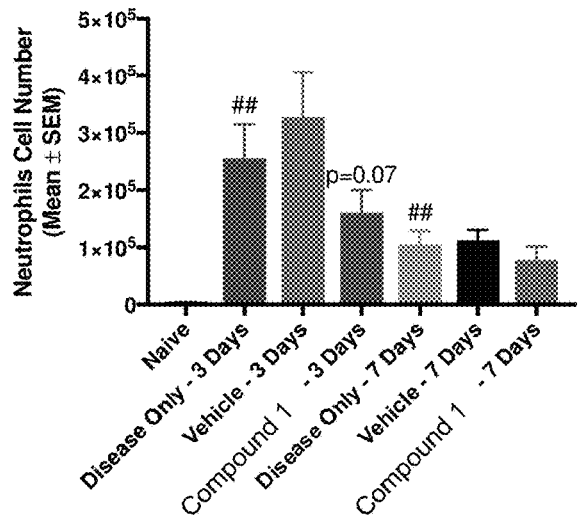
FIG. 3A depicts the number of neutrophils detected at the site of inflammation following sterile insult when treated with Compound 1.
Figure 3B:
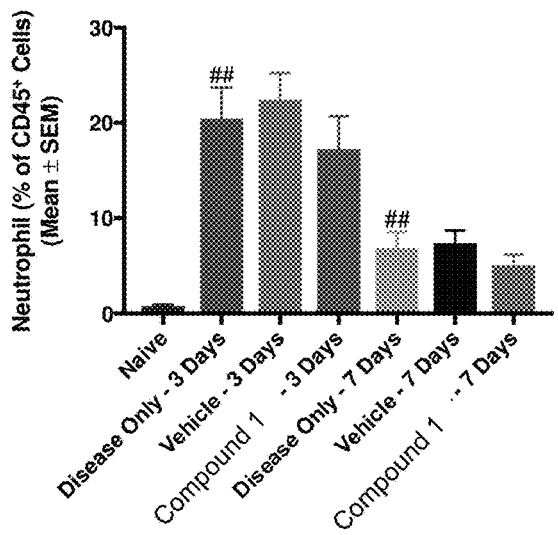
FIG. 3B depicts the amount of neutrophils expressed as percent of total leukocytes detected at the site of inflammation following sterile insult when treated with Compound 1.
Figure 4A:
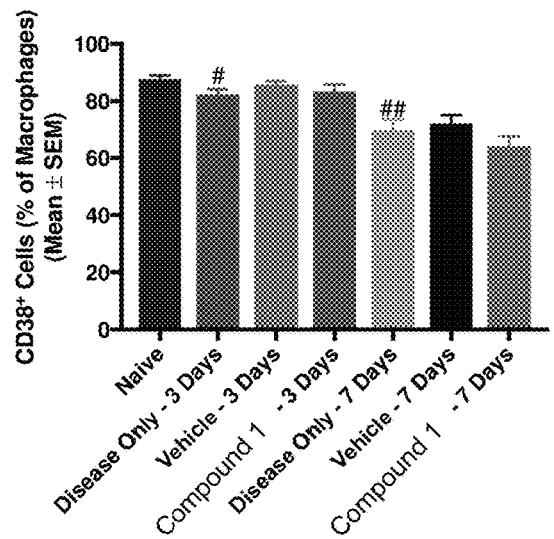
FIG. 4A depicts the amount of M1 macrophages expressed as a percentage of total macrophages detected at the site of inflammation following sterile insult when treated with Compound 1.
Figure 4B:
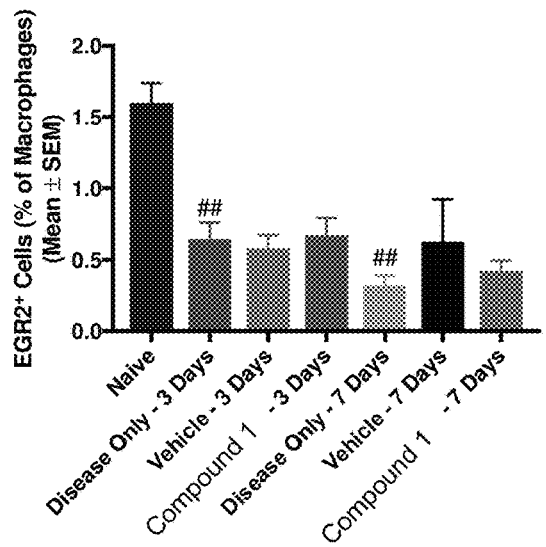
FIG. 4B depicts the amount of M2 macrophages expressed as a percentage of total macrophages detected at the site of inflammation following sterile insult when treated with Compound 1.

The number of neutrophils dropped significantly on day 7 in the disease only and vehicle tested animals, while the animals administered Compound 1 showed a less dramatic decrease (FIG. 3A). These results are reflected in FIG. 3B, which showed that the overall percentage of neutrophils relative to CD45+ leukocytes dropped significantly for all subjects.

Figure 5A:
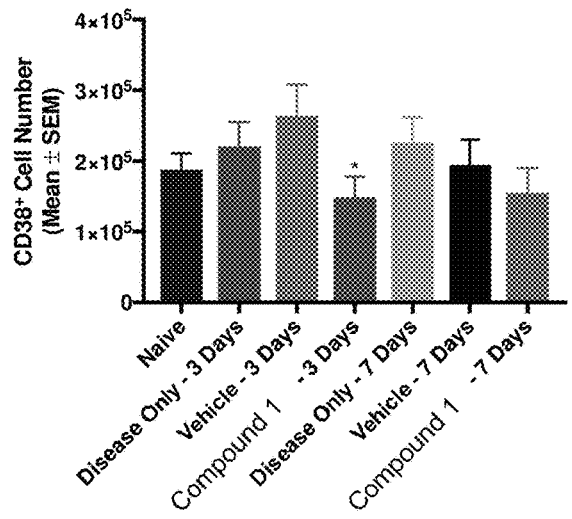
FIG. 5A depicts the number of M1 macrophages detected at the site of inflammation in the M2 activation state following sterile insult when treated with Compound 1.
Figure 5B:
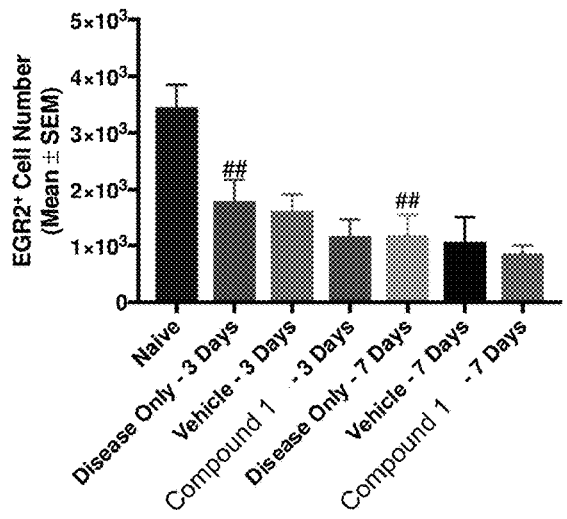
FIG. 5B depicts the number of M2 macrophages detected at the site of inflammation following sterile insult when treated with Compound 1.
Figure 6A:
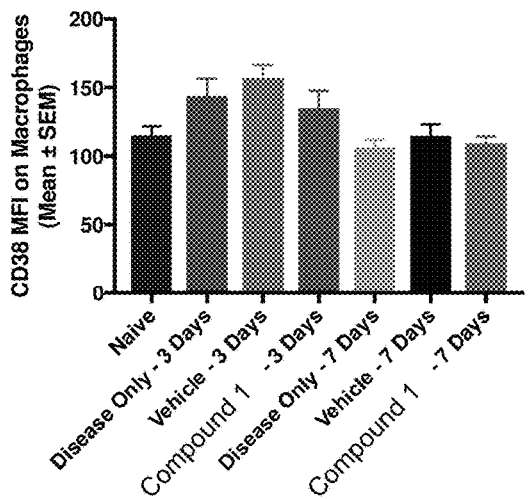
FIG. 6A depicts the mean fluorescent intensity (MFI) of CD38 expression on macrophage populations detected at the site of inflammation following sterile insult when treated with Compound 1.
Figure 6B:
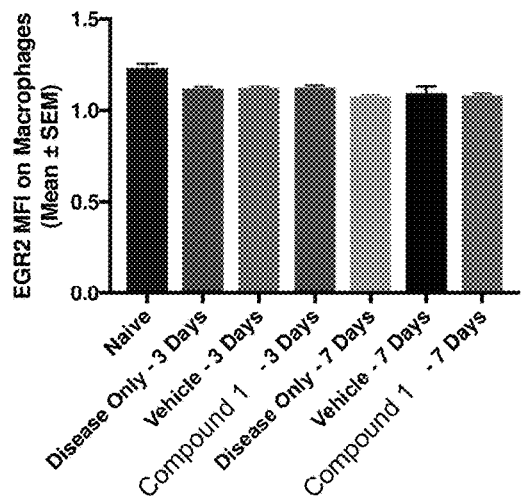
FIG. 6B depicts the mean fluorescent intensity (MFI) of CD38 expression on macrophage populations detected at the site of inflammation following sterile insult when treated with Compound 1.

To further assess the CD38 and Egr2 expression on macrophages, total numbers of CD38+ macrophages and Egr2+ macrophages were analyzed. Total numbers of CD38+ macrophages were increased in disease and vehicle day 3 animal groups, but decreased on day 3 for animals treated with Compound 1 (FIG. 5A). The number of Egr2+ macrophages was decreased for all animal groups at day 3 (FIG. 5B). The mean fluorescence intensity (MFI) of both CD38 and Egr2 was also analyzed on macrophages in FIGS. 6A and 6B. MFI provides a number that relates to the relative expression of a given marker on a cellular population. MFI for CD38+ showed an increase on day 3 for all animal groups, with the lowest value for the group treated with Compound 1, and decreased on day 7 for all groups. On the other hand, the MFI for Egr2+ was decreased on all animal groups on days 3 and 7, when compared to naïve.

Figure 7:
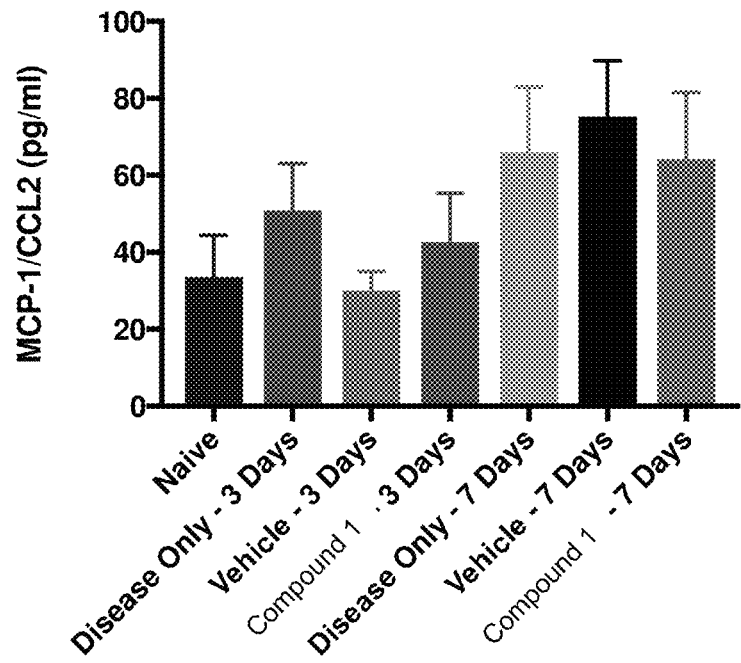
FIG. 7 depicts cytokine production in plasma in test subjects following sterile insult when treated with Compound 1.

Overall, the results indicate that the number of CD38+ cells tended to decrease and the number of Egr2+ cell number and percent tended to increase indicating a trend to increase the resolution phase of the inflammatory insult on day 7. As shown in FIG. 7, animals treated with Compound 1 also tended to show less inflammatory biomarkers (MCP-1/CCL2) at 3 and 7 days in comparison with control groups.

Figure 8:
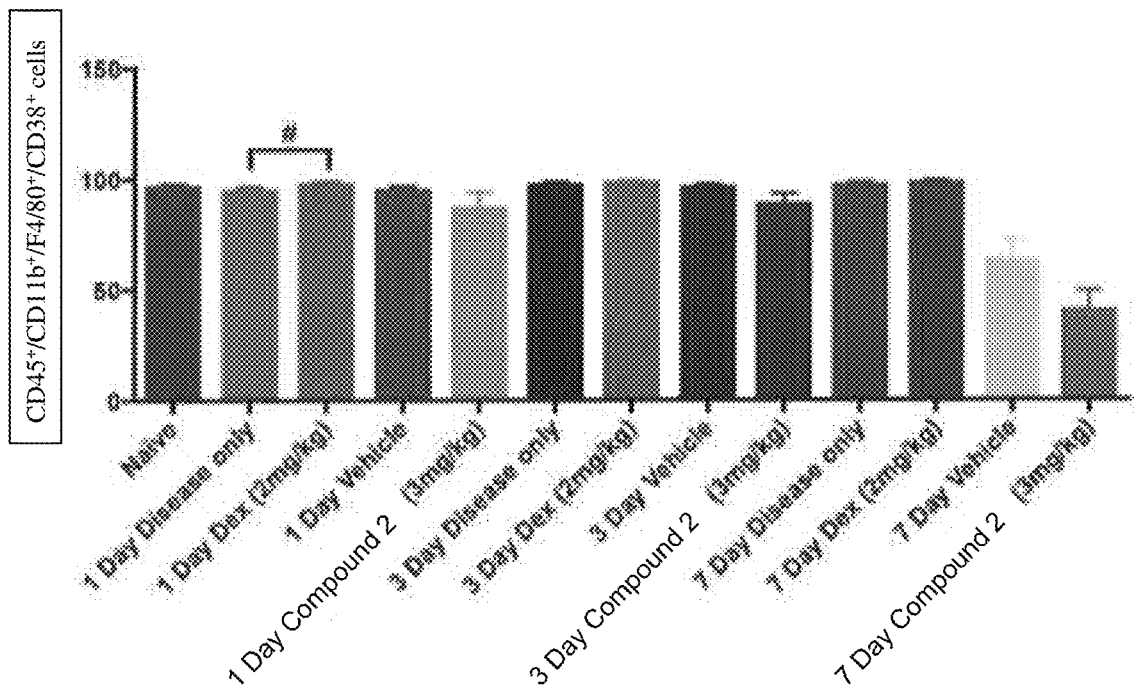
FIG. 8 depicts the number of macrophages in the M1 activation state detected at the site of inflammation following sterile insult when treated with Compound 2.
Figure 9:
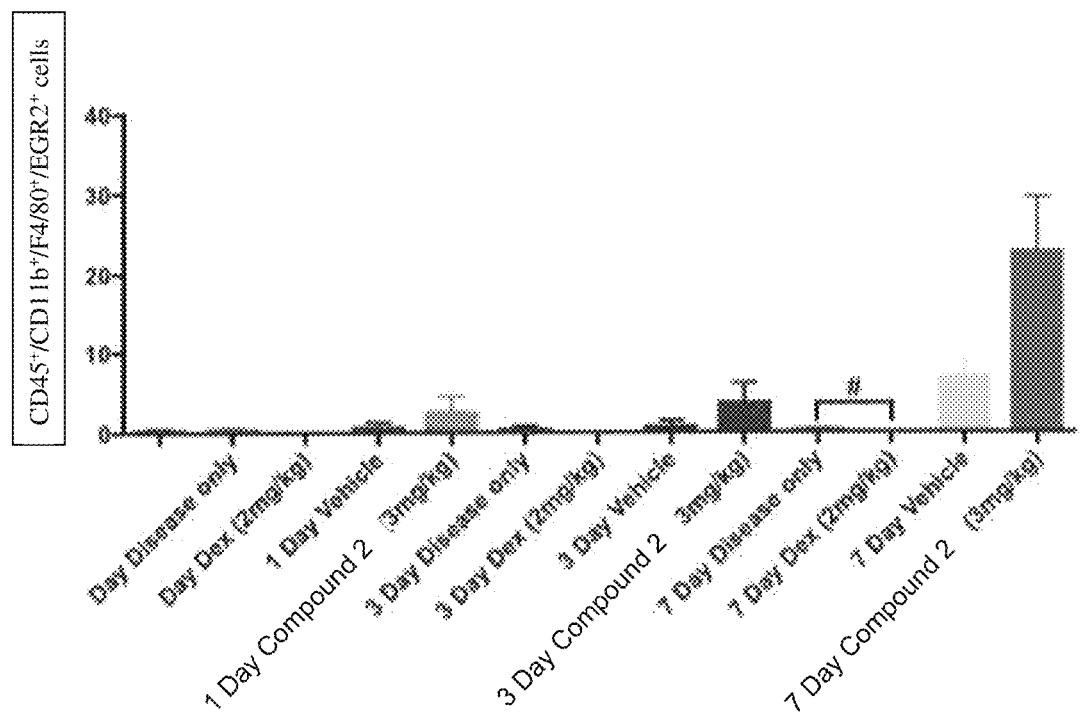
FIG. 9 depicts the number of macrophages in the M2 activation state detected at the site of inflammation following sterile insult when treated with Compound 2.

Similar tests were conducted with Compound 2, the results of which are illustrated in FIGS. 8 and 9. Treatment with 2 mg/kg of Dexamethasone had no significant effect on the number of CD38+ or Erg2+ macrophage populations on day 3 or 7. Treatment with 3 mg/kg of Compound 2, however, resulted in a significant drop of CD38+ macrophages, which corresponded with a sharp and significant increase in Erg2+ macrophages on day 7. An additional test was carried out according to the same method. Mice were injected intraperitoneally with 1 mg Zymosan followed by 10 mg/kg Compound 1. Macrophage levels were recorded at injection, then at 4, 8, 16, 24, 48 and 72 hours post-injection. The results are summarized in FIGS. 11A, 11B, 12A and 12B. As shown in FIGS. 11A and 11B, treatment with Compound 1 resulted in lower M1 macrophage levels at all observed times, with a significant different observed at day 7 in CD80+ macrophages. Correspondingly, Arg1+M2 macrophages increased at 4 hours, and CD206+M2 macrophages significantly increased at relative to control at 2 and 3 days.

Example 2: Effect of PDE1 Inhibitor on Microglia Chemotaxis Assay

Figure 10:
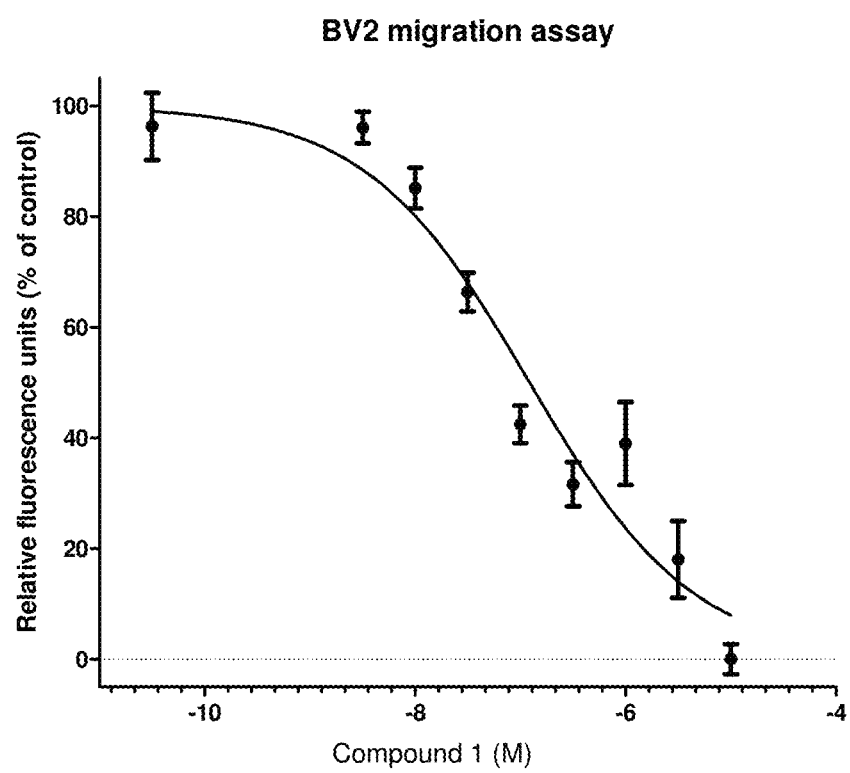
FIG. 10 depicts the results of Compound 1 on the motility of BV2 cells in a microglia chemotaxis assay.

BV2 cells were added to upper chamber of a 5 µm pore Transwell 96-well plate over a reservoir containing 100 µM ADP and incubated at 37° C. with 5% CO2 for 4 hours. After the incubation cells were harvested with pre-warmed cell detachment solution for 30 minutes in the same incubation conditions. 75 µl of this cell detachment solution was combined with 75 µl of culture medium in a new 96 well plate compatible with a fluorescence reader. Cell number in bottom chamber was determined by adding CyQuant® GR dye and reading in the Envision fluorescence reader at 480 nm EX/520 nm EM. CyQuant® GR dye exhibits strong fluorescence when bound to nucleic acid and is accurate enough to measure differences down to single cells. As shown in FIG. 10, the presence of the PDE1 inhibitor Compound 1 showed a marked dampening effect on the motility of the BV2 cells across the membrane, providing additional evidence that Compound 1 dampens the release of pro-inflammatory markers.

Example 3: Detection of Inflammatory Biomarkers Using Mouse Zymosan Pleurisy Model Zymosan was injected into the pleural cavities of mice in order to induce sterile inflammation by the methods discussed in Example 1. Compound 1 was administered to test subjects to observe the effects on a variety of inflammatory biomarkers. Results were recorded after 4 hours. The subjects showed a clear decrease in cytokine markers following administration of Compound 1. IFNγ, IL-1β, MCP1-β and TNF-α decreased following administration of Compound 1 in all serum and plasma samples. IL10 showed a decrease in serum.

Lipids are known to be involved in regulation of a multitude of cellular responses including cell growth and death, and inflammation/infection, via receptor-mediated pathways. Various lipids are involved in both the initiation and resolution of inflammation. Pro-resolving lipid mediators are produced naturally in the body from unsaturated fatty acids, such as arachidonic acid (AA) and docosahexaenoic acid (DHA). Further studies were carried out to identify metabolites of AA and DHA, which are summarized below in Tables 2 and 3.

TABLE 2

Detection of Arachidonic Acid Metabolites

| Metabolite | Inflammation Function | Result |
|---|---|---|
| TXB2 | Pro-inflammatory mediator | Decrease |
| PGE2 | Pro-inflammatory mediator | Decrease |
| LTB4 | Pro-inflammatory mediator | No change |
| 5-HETE | Intermediate mediator linked to resolution | No change |
| 12-HETE | Intermediate mediator linked to resolution | Increase |
| 15-HETE | Intermediate mediator linked to resolution | Increase |

TABLE 3

Detection of Docosahexaenoic Acid Metabolites

| Metabolite | Inflammation Function | Result |
|---|---|---|
| 17-HDOHE | Intermediate mediator linked to resolution | Increase |
| RVD5 | Intermediate mediator linked to resolution | Increase |
| 14-HDOHE | Resolution mediator | Increase |

As shown above in relation to AA metabolism, 12-HETE and 15-HETE, both intermediate mediators leading to resolution of inflammation, show increased occurrence compared with controls, while pro-inflammatory mediators TXB2, PGE2 and LTB4 all decrease. For the metabolism of DHA, each of 17-HDOHE, RVD5 and 14-HDOHE increase, all of which are related to resolution of inflammation. This profile of lipid biomarkers suggests that the tested compound induces metabolites of 15-LOX and 12-LOX pathways, indicating a mobilization of pro-resolution pathways. It also shows that the tested compound does not induce metabolites of 5-LOX, which is a pro-inflammatory pathway.

We claim:

1. A method of treatment of an inflammatory disease, condition or disorder consequent to a coronavirus infection, the method comprising administering a specific inhibitor of phosphodiesterase type I to a patient in need thereof, wherein the patient suffers from an inflammatory disease, condition or disorder consequent to a coronavirus infection, and wherein the inflammatory disease, condition or disorder is viral sepsis consequent to infection with SARS-COV-2, and wherein the PDE1 inhibitor is a compound selected from (A) Formula I

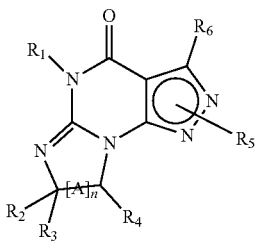

Formula I wherein
(i) $R_1$ is H or $C_{1-4}$ alkyl;
(ii) $R_4$ is H or $C_{1-4}$ alkyl and $R_2$ and $R_3$ are, independently, H or $C_{1-4}$ alkyl, aryl, heteroaryl, (optionally hetero) arylalkoxy, or (optionally hetero) arylalkyl; or
$R_2$ is H and $R_3$ and $R_4$ together form a di-, tri- or tetramethylene bridge;
(iii) $R_5$ is a substituted heteroarylalkyl;
or $R_5$ is attached to one of the nitrogens on the pyrazolo portion of Formula I and is a moiety of Formula A

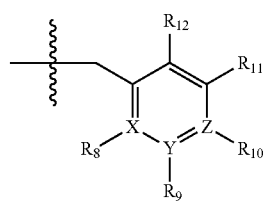

Formula A wherein X, Y and Z are, independently, N or C, and $R_8$, $R_9$, $R_{11}$ and $R_{12}$ are independently H or halogen, and $R_{10}$ is halogen, alkyl, cycloalkyl, haloalkyl, aryl, heteroaryl optionally substituted with halogen, or thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl, arylamino, heterarylamino, N,N-dialkylamino, N,N-diarylamino, or N-aryl-N-(arylalkyl) amino; and
(v) n=0 or 1;
(vi) when n=1, A is-C($R_{13}R_{14}$)—
wherein $R_{13}$ and $R_{14}$, are, independently, H or $C_{1-4}$ alkyl, aryl, heteroaryl, (optionally hetero) arylalkoxy or (optionally hetero) arylalkyl;
in free, salt or prodrug form, including its enantiomers, diastereoisomers and racemates;

(B) Formula Ia

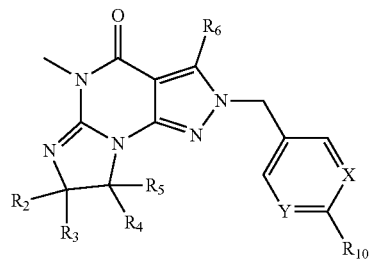

Formula Ia wherein
(i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;
(ii) $R_6$ is (optionally halo- or hydroxy-substituted) phenylamino, (optionally halo- or hydroxy-substituted) benzylamino, $C_{1-4}$alkyl, or $C_{1-4}$alkyl sulfide;
(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and
(iv) X and Y are independently C or N,
in free, pharmaceutically acceptable salt or prodrug form, including its enantiomers, diastereoisomers and racemates;

(C) Formula II

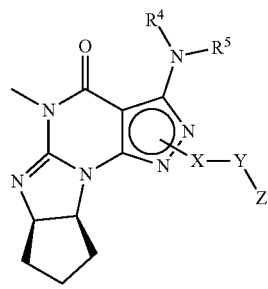

Formula II wherein
(i) X is $C_{1-6}$alkylene;
(ii) Y is a single bond, alkynylene, arylene or heteroarylene;
(iii) Z is H, aryl, heteroaryl, halo, halo$C_{1-6}$alkyl, —C(O)—$R^1$, —N($R^2$) ($R^3$), or $C_{3-7}$cycloalkyl optionally containing at least one atom selected from a group consisting of N or O;

(iv) $R^1$ is $C_{1-6}$alkyl, halo$C_{1-6}$alkyl, —OH or —O$C_{1-6}$alkyl;
(v) $R^2$ and $R^3$ are independently H or $C_{1-6}$alkyl;
(vi) $R^4$ and $R^5$ are independently H, $C_{1-6}$alkyl or aryl optionally substituted with one or more halo, hydroxy or $C_{1-6}$alkoxy;
(vii) wherein X, Y and Z are independently and optionally substituted with one or more halo, $C_{1-6}$alkyl, halo$C_{1-6}$alkyl,
in free, salt or prodrug form;

(D) Formula III

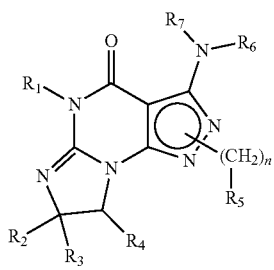

Formula III wherein
(i) R1 is H or $C_{1-4}$ alkyl;
(ii) $R_2$ and $R_3$ are independently H or $C_{1-6}$ alkyl;
(iii) $R_4$ is H or $C_{1-4}$ alkyl;
(iv) $R_5$ is aryl optionally substituted with one or more groups independently selected from —C(=O)—$C_{1-6}$ alkyl;
(v) $R_6$ and $R_7$ are independently H or aryl optionally substituted with one or more groups independently selected from $C_{1-6}$ alkyl and halogen; and
(vi) n is 1, 2, 3, or 4,
in free or salt form;

(E) Formula IV

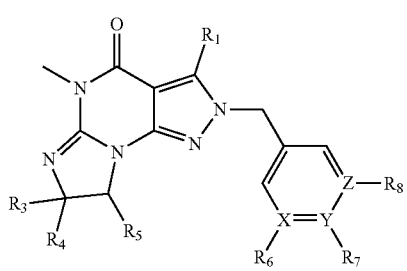

Formula IV in free or salt form, wherein
(i) $R_1$ is $C_{1-4}$alkyl, or —NH($R_2$), wherein $R_2$ is phenyl optionally substituted with halo;
(ii) X, Y and Z are, independently, N or C;
(iii) $R_3$, $R_4$ and $R_5$ are independently H or $C_{1-4}$alkyl; or $R_3$ is H and $R_4$ and $R_5$ together form a tri-methylene bridge,
(iv) $R_6$, $R_7$ and $R_8$ are independently:
H,
$C_{1-4}$alkyl,
pyrid-2-yl substituted with hydroxy, or
—S(O)$_2$—NH$_2$;
(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy, (F) Formula V

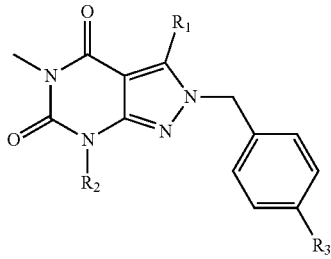

Formula V wherein
(i) $R_1$ is —NH($R_4$), wherein $R_4$ is phenyl optionally substituted with halo;
(ii) $R_2$ is H or $C_{1-6}$alkyl;
(iii) $R_3$ is —SO$_2$NH$_2$ or —COOH;
in free or salt form; and (G) Formula VI

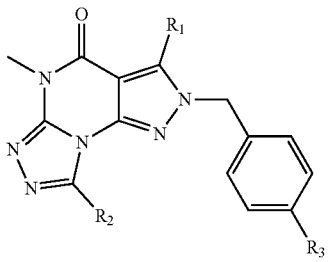

Formula VI wherein
(i) $R_1$ is —NH($R_4$), wherein $R_4$ is phenyl optionally substituted with halo;
(ii) $R_2$ is H or $C_{1-6}$alkyl;
(iii) $R_3$ is H, halogen, $C_{1-6}$alkyl, aryl optionally substituted with halogen, heteroaryl optionally substituted with halogen, or acyl,
in free or pharmaceutically acceptable salt form.

2. The method according to claim 1, wherein the patient has
a. elevated levels of one or more pro-inflammatory cytokines;
b. reduced levels of one or more anti-inflammatory cytokines;
c. elevated levels of macrophages of the M1 phenotype compared to macrophages of the M2 phenotype; and/or
d. reduced levels of T-cells or increased levels of exhausted T-cells.

3. The method according to claim 1, wherein the PDE1 inhibitor is the following:

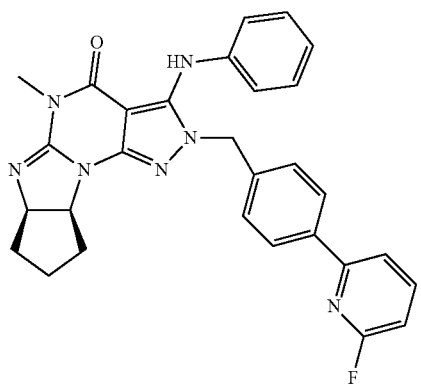 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

4. The method according to claim 1, wherein the PDE1 inhibitor is the following:

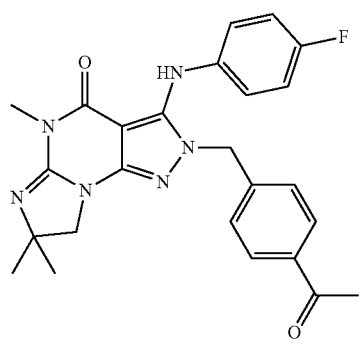 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

5. The method according to claim 1, wherein the PDE1 inhibitor is the following:

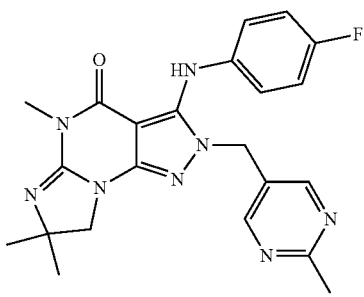 [SMILES: Cc1ncc(Cn2nc3c(c2Nc2ccc(F)cc2)C(=O)N(C)C2=NC(C)(C)CN23)cn1]

in free or pharmaceutically acceptable salt form.

6. The method according to claim 1, wherein the PDE1 inhibitor is the following:

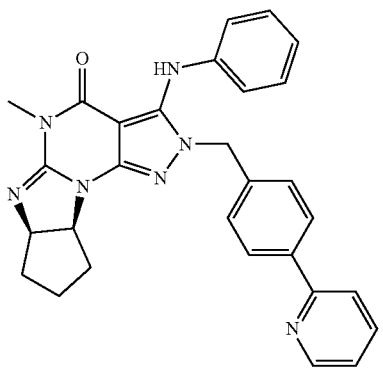 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

7. The method according to claim 1, wherein the PDE1 inhibitor is administered in combination with a PDE4 inhibitor.

* * * * *